US008784327B2

(12) United States Patent
Heim

(10) Patent No.: US 8,784,327 B2
(45) Date of Patent: Jul. 22, 2014

(54) METHOD AND SYSTEM FOR OBTAINING DIMENSION RELATED INFORMATION FOR A FLOW CHANNEL

(75) Inventor: Warren P. Heim, Boulder, CO (US)

(73) Assignee: Team Medical, LLC, Boulder, CO (US)

( * ) Notice: Subject to any disclaimer, the term of this patent is extended or adjusted under 35 U.S.C. 154(b) by 1063 days.

(21) Appl. No.: 12/372,565

(22) Filed: Feb. 17, 2009

(65) Prior Publication Data

US 2009/0149765 A1     Jun. 11, 2009

Related U.S. Application Data

(62) Division of application No. 10/268,113, filed on Oct. 9, 2002, now Pat. No. 7,491,173.

(60) Provisional application No. 60/345,700, filed on Jan. 4, 2002, provisional application No. 60/328,625, filed on Oct. 10, 2001.

(51) Int. Cl.
*A61B 5/02*         (2006.01)

(52) U.S. Cl.
USPC ............................................ 600/504

(58) Field of Classification Search
USPC ............................................ 600/504
See application file for complete search history.

(56) References Cited

U.S. PATENT DOCUMENTS

| | | | | |
|---|---|---|---|---|
| 4,493,216 A | * | 1/1985 | Hassler | 73/861.25 |
| 4,733,669 A | * | 3/1988 | Segal | 600/585 |
| 4,796,634 A | * | 1/1989 | Huntsman et al. | 600/457 |

* cited by examiner

*Primary Examiner* — Michael D'Angelo
*Assistant Examiner* — Christian Jang
(74) *Attorney, Agent, or Firm* — Marsh Fischmann & Breyfogle LLP; Kent A. Fischmann

(57) ABSTRACT

A method and system for determination of dimension related information such as volumetric flow rate(s) of a fluid flowing through a channel. In one implementation, the method and system analyzes temporal changes in a moving fluid's velocity profile to calculate the fluid channel dimensions. In turn, the fluid channel dimensions and the fluid velocity profile data may be combined to calculate the volumetric flow rate of the fluid flowing through the channel. In this regard, the geometry of the channel can be characterized using dimensionless variables that relate dimensions, such as the radius across a circular cross-section, to the largest extent of a dimension. For example, in the case where the channel is a cylindrical tube and a pressure gradient is applied long enough for the fluid to have reached a steady state, the dimensionless radius will be the radius at any point divided by the overall radius of the tube. One or more dimensionless variables can be used to characterize geometries: for instance, one dimensionless radius characterizes a circular tube and two dimensionless terms characterize an elliptical tube (one for the major axis and one for the minor axis). The time required for velocity profiles to change from one shape to another may be characterized by dimensionless time. Dimensionless time, in turn, uses the fluid's viscosity and density along with time and overall channel dimensions and may be used in combination with at least one velocity profile to calculate the volumetric flow rate of the fluid flowing through the channel.

5 Claims, 19 Drawing Sheets

METHOD AND SYSTEM FOR OBTAINING DIMENSION RELATED INFORMATION FOR A FLOW CHANNEL

RELATED APPLICATION INFORMATION

This application is a divisional of U.S. patent application Ser. No. 10/268,113, filed Oct. 9, 2002, which claims priority from U.S. Provisional Patent Application Ser. No. 60/345,700, filed Jan. 4, 2002, and U.S. Provisional Patent Application Ser. No. 60/328,625, filed on Oct. 10, 2001, and which are incorporated herein by reference in their entirety.

FIELD OF THE INVENTION

The present invention relates to a method and system for determining channel dimension related information based on measurements performed on a fluid flowing through a channel of unknown dimensions. The invention allows for using a non-invasive interrogating signal to obtain substantially real-time velocity measurements and, in turn, to use such measurements to assess properties of the channel containing the fluid, including instantaneous volumetric flow rate.

BACKGROUND OF THE INVENTION

In a variety of contexts, it is desirable to obtain dimension related information for a flow channel where it is difficult or undesirable to access the flow channel or otherwise obtain a direct dimensional measurement. Obtaining such information is particularly challenging where channel dimensions vary over time. An example is obtaining dimension related information for a blood vessel (i.e., artery or vein), such as the ascending aorta, of a human or other patient. The dimension related information of interest may be a dimension of the flow channel or other information derived from or dependent on dimension such as quantitative flow rate information (e.g., volumetric or mass flow rate), vessel elasticity/health, volumetric delivery per heartbeat, ejection fraction or the like.

A channel dimension related characteristic of particular interest is volumetric flow rate ("VFR"). The volumetric flow rate ("VFR") of a fluid flowing through a channel is dependent on the velocity of the fluid and the cross-sectional area of the channel. Instantaneous VFRs may be calculated when these values are known between short time intervals that may be considered instantaneous. Determining the VFR of fluids in patients is useful, for example, in assessing cardiac performance. In this application, the fluid is a liquid, e.g., blood, that is flowing through a closed channel, such as the aorta. Unfortunately, variability between individual patients prevents knowing the dimensions of a channel inside the patient absent a measurement to determine the channel dimensions.

Presently, the principle technologies used to measure cardiac blood flow employ time-varying markers, such as a dye, chilled normal saline, or blood warmed with a small electric heater, introduced into the heart through a catheter. The rate of change of the marker is then used to estimate the overall flow rate of blood. The catheter is most commonly introduced into the patient's femoral artery and threaded through the venous system into and through the heart to the pulmonary artery. A variant of this method introduces a dye without a catheter, but requires an injection near the atrium and measures the dye concentration at a point such as the ear. Unfortunately, these time-varying marker methods rely on the marker dilution transient and provide bulk flow data, rather than flow rate data through a channel. In addition, the time-varying marker methods do not provide instantaneous VFRs.

Another group of methods for measuring cardiac flow, known as "Fick methods," calculate cardiac output using the difference in oxygen content between the arterial and mixed venous blood and the total body oxygen consumption. The classic Fick method uses arterial and pulmonary artery catheters to measure the oxygen content. Related methods measure oxygen and carbon dioxide data in a patient's airways to avoid using catheters. However, similar to the time-varying marker methods, Fick methods measure bulk cardiac output, and not flow rates. Finally, other methods, such as bioimpedance, may also be used to measure cardiac output. However, as with the Fick methods and time-varying marker methods, these methods do not measure flow rate, but rather only cardiac output.

Certain methods exist for non-invasively determining fluid velocities, with Doppler methods being the most common in the context of blood flow analysis. Such methods, however, only measure fluid velocity and require another measurement to provide the channel dimensions if quantitative flow rate information is desired. Such channel dimension measurements have sometimes been obtained based on methods related to imaging or time delays. X-rays and radiopaque dyes may also be used, but the results are time consuming and difficult to interpret. Further, the time-delay of echoes from an ultrasound signal may be used to provide an estimate of the channel dimensions, but obtaining precise results has required disposing the ultrasonic transducers in close proximity to the channel, something that is not possible unless the devices are introduced into the patient. Therefore, significant deficiencies exist in relation to non-invasive determination of a VFR of fluid in a channel.

Conventional flow channel measurements may also be problematic, uncertain or inaccurate due to measurement artifact and associated processing. For example, ultrasound measurements of an ascending aorta are problematic due to the difficulty of isolating the signal of interest from measurement artifact. Such artifact may relate to echoes from physiological material outside of the aorta or other channel that tend to obscure the signal of interest, in-channel noise sources and other interfering components. Some approaches have attempted to minimize certain artifact components by disposing the probe in close proximity to the aorta, thus incurring a morbidity trade-off. Other approaches attempt to minimize certain artifact components by employing a very narrow signal, but thereby complicate targeting of the aorta or other channel under consideration.

SUMMARY OF THE INVENTION

In view of the foregoing, a broad objective of the present invention is to provide a method and system for obtaining dimension related information for a flow channel, including a flow channel of a patient such as a blood vessel, based on qualitative flow rate information, e.g., velocity measurements. A related objective involves determining a quantitative flow rate such as a volumetric flow rate(s) ("VFR") of a fluid flowing through a channel. Another object of the present invention is to provide a method and system for non-invasive determination of a VFR of a fluid (e.g. blood) flowing through a living patient. A further related object is to provide a non-invasive method and system for determining fluid channel dimensions and combining the fluid channel dimension data with fluid velocity data to determine instantaneous VFR data. In particular, an object of the present invention is to use the same signals to measure fluid velocity data and determine fluid channel dimensions. A still further object of the present invention is to noninvasively obtain substantially real time velocity related and dimensional information for a flow channel such as a blood vessel, so as to enable instantaneous qualitative flow rate information, including for channels having dimensions that vary with time. It is also an object of the present invention to accurately account for artifacts associated with measurements related to a flow channel. Another object of the present invention is to provide for a rapid computation of otherwise computationally intractable formulae.

In the medical context, the present invention allows for determining dimension related information for a flow channel without introducing a probe into the patient, thereby reducing pain and discomfort and reducing the likelihood of other problems such as the possibility of infection. Additionally, the present invention allows for obtaining such a measurement quickly, simply and at a reasonable cost. The present invention also enables measurements that can be used to determine instantaneous VFRs to enable clinicians to examine temporal changes and combine VFR measurements with other vital sign measurements, such as an electrocardiogram (EKG) measurement.

According to one aspect of the present invention, flow characteristic information for a flow of a physiological material in a patient is used to obtain processed information related to a dimension of a flow channel. This aspect of the invention may be implemented as a process performed, at least in part, by a processor, and may be embodied, for example, in a software product or other logic, a processing unit for executing such logic, or a system for use in performing associated medical procedures.

In one implementation, the flow characteristic information is qualitative flow characteristic information, i.e., information related to a flow velocity or derivatives thereof. For example, flow velocity may be invasively or noninvasively measured at one or more points relative to a cross-section of a channel. Such flow velocity measurements may be used to calculate derivative information such as average flow velocity for that channel cross-section or information related to change in velocity relative to a channel dimension such as radius. The flow velocity measurements may also be used in calculating other parameters that characterize an instantaneous velocity profile. Such measurements may be repeated to provide derivative information related to a temporal change in velocity profile. It will thus be appreciated that the flow characteristic information may be provided in various forms, or be characterized by different parameters. Moreover, the flow characteristic information may be based on a single or multiple measurements performed with respect to the flow channel under consideration. Additionally, such flow characteristic information may be used in multiple steps of a calculation, e.g., velocity profile information may be used to derive first processed information such as dimension related information, and the first processed information may be combined with average velocity or other flow characteristic information to derive second processed information.

The manner of obtaining such information can vary depending on the particular inventive implementation under consideration. For example, in the case of software product or processor implementation, such information may be obtained in the form of an analog or digital signal, received either directly from a measurement device or via intervening processing. In medical system implementations, the flow characteristic information may be obtained by performing medical procedures on a patient. In this regard, information such as flow velocity measurements may be obtained invasively, e.g., by introducing measurement elements into the flow channel or positioning a probe within the patient adjacent to the flow channel, or noninvasively, e.g., by receiving a signal from the channel such as an echo signal in the case of ultrasound modalities. The obtainment of such information can be synchronized with physiological processes of interest in accordance with the present invention.

The processed information obtained using the flow characteristic information can vary depending on the application under consideration. Such information may include, for example, dimensional information regarding the flow channel such as a radius, major/minor axis dimension(s), cross-sectional area or other parameters characteristic of channel dimension; information derived from dimensional information such as a quantitative flow rate; or information otherwise dependent on such dimensional information (even if dimensional information is not determined as an intermediate step). Examples of medical information that may be obtained in this regard include: the area, volumetric flow rate, pressure gradient, blood volume over time period of interest or elasticity of a blood vessel; and a cardiac pumping cycle period, volumetric delivery or ventricle ejection fraction of a patient.

An application of particular interest relates to determining the volumetric flow rate of a fluid channel such as an ascending aorta of a patient. The present inventor has recognized that temporal changes in a moving fluid's velocity profile can be analyzed to calculate dimensions of a fluid channel. In turn, the fluid channel dimensions and the fluid velocity profile data can be combined to calculate a VFR for the fluid flowing in the channel.

In this regard, unsteady laminar flow along the length of a channel contains fluid elements moving at velocities that depend upon their distance from the channel walls, the channel geometry, the pressure gradient acting on the fluid, the fluid properties, and the initial velocities of the fluid elements. The fluid elements directly contacting the channel walls do not move and have $v=0$, where $v$ is the velocity along the length of the channel. The velocities of fluid elements away from the channel walls regularly transition to velocities that depend upon the distance from the channel walls. When the pressure gradient does not reverse direction, the velocities of the fluid elements that are farthest from the walls are the greatest. The shape and dimensions of the pattern that these fluid velocities take in relation to the geometry of the channel defines a velocity profile.

The present inventor has also recognized that the geometry of the channel can be characterized using one or more dimensionless variables that relate dimensional values, such as a given point on the radius across a circular cross-section, to the largest extent of the dimension under consideration. For example, in the case where the channel is a cylindrical tube, the dimensionless radius can be defined as the radius at any point divided by the overall radius of the tube. One or more dimensionless variables can be used to characterize geometries, e.g. one dimensionless radius characterizes a circular tube and two dimensionless axes characterize an elliptical tube (one for the major axis and one for the minor axis). More complicated geometries can be represented by multivariate functions or the like. The time required for velocity profiles to change from one shape to another may be characterized by dimensionless time. A definition of dimensionless time, as discussed below, involves the fluid's viscosity and density along with time and overall channel dimensions.

In this regard, a further aspect of the present invention is directed to a method for externally measuring a velocity of a fluid flowing through a channel. The method entails measuring the velocity of the fluid flowing through the channel using a non-invasive means such as an interrogating signal. In turn, the measured velocity is used to calculate an area of the channel, e.g. a cross-sectional area, which is then utilized along with the measured velocity to calculate at least one VFR for the fluid flowing through the channel.

Various refinements exist of the features noted in relation to the subject aspect. Further features may also be incorporated into the subject aspect to form multiple examples of the present invention. These refinements and additional features will be apparent from the following description and may exist individually or in any combination. For instance, the velocity of the fluid may be measured using an ultrasonic interrogating signal. Such a velocity measurement may be characterized by a velocity profile. A velocity profile function, in turn, may be used to calculate velocity profile parameters for the velocity profile at a first time. The velocity profile parameters may then be utilized to calculate a mean velocity of the fluid flowing through the channel. A dimensionless time may be calculated using the velocity profile parameters and a functional relationship characterizing how velocity profiles change with time. The dimensionless time, in turn, is related to the dimensions of the channel such that the dimensions of the channel may be calculated and used to determine a cross-sectional area of the channel. The cross-sectional area of the channel may be utilized with the mean fluid velocity to determine at least one VFR for the fluid flowing through the channel. In this regard, errors in the velocity measurement may be accounted for by distinguishing between signals emanating from the moving fluid and signals emanating from surrounding regions that may produce signal noise that would otherwise confound determining the correct velocity profile and fluid channel dimensions. Further in this regard, random measurement errors may be absorbed such that the errors can be discriminated from the actual velocity profile.

According to a further aspect of the invention, a system for calculating VFRs is provided. The system includes a data processor that uses a measured fluid velocity to calculate an area of a channel and uses the area of the channel and the measured fluid velocity to calculate at least one VFR for the fluid flowing through the channel. The system may further include one or more output modules to provide an output to a user indicative of at least one volumetric flow rate. The system may further include a velocity measuring device to measure the fluid velocity and provide the measured velocity to the data processor. In this regard, the data processor may include logic for calculating channel dimensions using two or more flow velocity profiles or velocity flow distributions, and logic for using channel dimension data in conjunction with measured velocity data to calculate at least one VFR.

Various refinements exist of the features noted in relation to the subject aspect. Further features may also be incorporated into the subject aspect to form multiple examples of the present invention. These refinements and additional features will be apparent from the following description and may exist individually or in any combination. For instance, such a system can also include logic for discriminating the flow velocity distribution from measured data that also includes data other than that associated with the material flowing in a channel. Such a system can also include logic for calculating pressure gradients and other derived parameters such as the rate of change of VFR's or measures of channel elasticity that relate channel dimensions and pressure gradients. The data processor will typically be one or more electronic devices that use one or more semiconductor components such as microprocessors, microcontrollers, or memory elements. The data processor will typically have a data storage element, employing non-volatile memory means, such as one or more magnetic media (such as disk drives), optical media (such as CD ROM), or semiconductor means (such as EPROM or EEPROM). The data storage element could be used, for example, to store data used to facilitate computations. Examples of data that may be stored to facilitate computations include without limitation, data stored for avoiding or reducing the need to calculate special functions, such as Bessel, Lommel, Bessell-zero, modified Bessel, Gamma, log-Gamma, and hypergeometric functions.

In one embodiment of the system, the velocity measurement device may use an interrogating signal that is transmitted into the region containing the channel with the flowing fluid for which the VFR or other parameters are to be determined. Such an interrogating signal may use transmitted energy that has amplitudes that vary with time, such as ultrasonic energy or electromagnetic energy (including light that is in the visible spectrum as well as electromagnetic radiation that has frequencies below or above the visible spectrum). Ultrasonic energy will typically use frequencies in the range between 50 kHz and 50 MHz and more typically in the range between 500 kHz and 5 MHz. Such interrogating signals may be sent either continuously or in pulses. The velocity measurement device can use changes in velocity or phase that occur when the interrogating signal interacts with moving material that either backscatters energy or produces echoes. One example of such an embodiment includes without limitation, Doppler measurements.

A system for calculating VFRs may further include logic for timing measurements based on external signals. Such external timing signals include those related to flow inducing phenomena such as signals related to factors that cause pressure gradient changes. For example, the system can use signals related to a heart's electrical activity, such as electrocardiograph (EKG) signals, to sequence or control when measurements are made or to correlate measurements. In this regard, controlling when measurements are made can influence when interrogation signals are transmitted and correlating measurements can influence how measurements that have been made are interpreted.

The one or more data output modules may be of any suitable type such as displays, audible sound producing elements, or data output ports such as those that transmit electronic or electromagnetic signals and associated local or wide-area network ports. The system may also include one or more controls such as power controls, signal sensitivity adjustments, or adjustments that cause signals or calculated results to be altered based on the characteristics of the flowing medium. Such adjustments may include those that are based on fluid properties and include adjustments for standard fluid properties. Some examples of such standard fluid properties include without limitation, viscosity, density, and kinematic viscosity. Adjustments based on fluid property can include properties correlated with standard fluid properties and include hematocrit as a correlated fluid property. Adjustments based on hematocrit can include using single values of hematocrit, ranges of hematocrit, or patient-specific data that are related to hematocrit such as patient species, age, or sex.

According to another aspect of the invention a software product for calculating dimension related information for a fluid channel is provided. The software product includes data processor instructions that are executed on a processor, e.g. a data processor, to use a measured flow characteristic such as information related to fluid velocity to calculate dimension related information, such as a channel radius or area for a channel. The software product may further include instructions for using dimension related information together with the measured flow characteristic to calculate at least one additional value, which may be a further dimension related value such as a VFR for the fluid flowing through the channel. The software product may further include output instructions configured to provide an output to a user indicative of at least one of the flow characteristic, the dimension related information and the additional value. The software product may further include velocity measuring instructions for obtaining a measurement of the fluid velocity and providing the measured velocity to the data processor. In this regard, the data processor instructions may be configured to calculate channel dimensions using two or more flow velocity profiles or velocity flow distributions, and instructions for using channel dimension data in conjunction with measured velocity data to calculate at least one VFR.

Various refinements exist of the features noted in relation to the subject aspect. Further features may also be incorporated into the subject aspect to form multiple examples of the present invention. These refinements and additional features will be apparent from the following description and may exist individually or in any combination. For instance, such a software product may also include instructions for discriminating the flow velocity distribution from measured data that also includes data other than that associated with the material flowing in a channel. Such a software product can also include instructions for calculating pressure gradients and other derived parameters such as the rate of change of VFR's or measures of channel elasticity that relate channel dimensions and pressure gradients.

A software product for calculating VFRs may further include instructions for timing measurements based on external signals. As discussed above, such external timing signals may include those related to flow inducing phenomena such as signals related to factors that cause pressure gradient changes. For example, the software product could use signals related to a heart's electrical activity, such as electrocardiograph (EKG) signals, to sequence or control when measurements are made or to correlate measurements.

According to a still further aspect of the present invention, substantially real-time velocity measurements and substantially real-time dimension related information are obtained for a patient flow channel at substantially the same time. In each case, the information may be obtained noninvasively such as by ultrasound processes based on the same or multiple signal sets. For example, ultrasound measurements may be used, as discussed above, to obtain velocity profile information at successive times and information related to the temporal change in velocity profile may be used to derive dimension related information. From the velocity measurements and/or initial dimension related information, additional dimension related information such as a VFR value or other derived information may be obtained. In this regard, the successive velocity profile measurements may be made sufficiently close in time that other flow parameters such as channel cross-section and pressure gradient, may safely be assumed unchanged, or successive measurements may be pulse cycle synchronized and/or variations in other flow parameters may be taken into account. In any event, instantaneous results can be obtained, allowing for more timely presentation to physicians and improved correlation to physiological processes as may be desired.

According to another aspect of the invention, a method and apparatus are provided to account for artifacts in a signal used to determine information regarding a physiological material in motion, for example, a physiological fluid in a flow channel of a patient. The present inventor has recognized that such artifacts may relate to signal portions associated with surrounding material or noise associated with signal portions emanating from the flow channel. Some prior attempts to address artifacts have recognized, for example, that a spectral analysis of ultrasound information related to a flow channel exhibits bimodal characteristics but have assumed that frequency filtering can be employed to isolate a spectral portion of interest without introducing unacceptable inaccuracies. In accordance with the present invention, a mathematical model is provided that characterizes the input signal as a signal portion of interest and an undesired signal component. An analysis is then employed using the mathematical structure to mathematically absorb the undesired signal portion free from frequency filtering and the associated assumptions. For example, multi-parameter functions may be used to parameterize the input signal including the undesired signal portion and well-founded statistical processes can be used to absorb the undesired components. In this manner, either or both of in-channel and out-of-channel artifact can be absorbed. This allows for improved accuracy of results as well as relaxed requirements for targeting interrogation signals at a flow channel. In the latter regard, standard ultrasound measurements or more advanced measurements as disclosed herein, may be accurately performed without positioning the probe within the patient adjacent to the channel, or without targeting complications associated with very narrow signals.

DESCRIPTION OF THE DRAWINGS

For a more complete understanding of the present invention and further advantages thereof, reference is now made to the following detailed description, taken in conjunction with the drawings, in which.

DETAILED DESCRIPTION

Reference will now be made to the accompanying drawings, which at least assist in illustrating the various pertinent features of the present invention. Although the present invention will now be described primarily in conjunction determining VFR's of a fluid, e.g. blood, flowing through a channel, e.g. an artery, of a patient, it should be expressly understood that the present invention is not limited to this application, but rather, is useful in a variety of applications related to performing measurements on moving physiological material and other flow measurement applications, especially where direct access to the flow channel is difficult or otherwise undesirable or problematic. Consequently, variations and modifications commensurate with the following teachings, and skill and knowledge of the relevant art, are within the scope of the present invention. The embodiments described herein are further intended to explain best modes known of practicing the invention and to enable others skilled in the art to utilize the invention in such, or other embodiments and with various modifications required by the particular application(s) or use(s) of the present invention.

Figure 1:
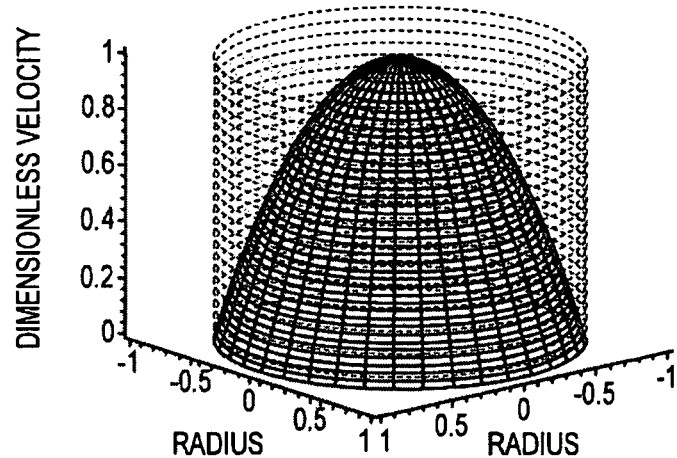
FIG. 1 illustrates the dimensionless velocity profile for fully developed laminar flow.

As noted above, unsteady laminar flow along the length of a channel contains fluid elements moving at velocities that depend upon their distance from the channel's walls, the channel's geometry, the pressure gradient acting on the fluid, the fluid's properties, and the initial velocities of the fluid elements. The fluid elements directly contacting the channel's walls do not move and have v=0, where v is the velocity along the length of the channel. The velocities of fluid elements away from the channel's walls regularly transition to velocities that depend upon the distance from the channel's walls. When the pressure gradient does not reverse direction the velocity of the fluid elements in that are farthest from the walls move the fastest. FIG. 1 illustrates the velocities for the case where the channel is a cylindrical tube and the pressure gradient has been applied long enough for the fluid flow to have reached steady state. The shape and dimensions of the pattern that the velocities of the fluid elements take in relation to the geometry of the channel is the velocity profile.

In this regard, the geometry of the channel can be characterized using dimensionless variables that relate dimension values, such as a value of a particular position relative to the radius across a circular cross-section, to the largest extent of the dimension under consideration. For example, the dimensionless radius may be defined as the radius at any point divided by the overall radius of the tube. One or more dimensionless variables can be used to characterize geometries: one dimensionless radius characterizes a circular tube and two dimensionless axes characterize an elliptical tube (one for the major axis and one for the minor axis). In some cases proxies for a dimensionless variable may be used, such as aspect ratio wherein the aspect ratio is the ratio of major axis to minor axis in an ellipse, and which may be used in conjunction with the major dimensionless axis.

The time required for velocity profiles to change from one shape to another may be characterized by dimensionless time. A definition of dimensionless time uses the fluid's viscosity and density along with time and overall channel dimensions. In this regard, the general form of dimensionless time is $$\tau = \frac{\mu t}{\rho f(D)}$$

where $\mu$=viscosity, $\rho$=density, t=time, and f(D) is a function of the parameters that characterize the channel's dimensions. f(D) has the dimensions of length-squared ($L^2$).

Dimensionless time, $\tau$, is also called a time constant and may be used to evaluate how many time constants are needed for a certain event to occur. For example, blood flow in humans in the aorta follows a cyclic pattern determined by the heart rate. Typically, the heartbeat to heartbeat cycle lasts about 0.01 and 0.1 time constants (where the time constant utilized is described in greater detail below), and in most cases lasts between about 0.01 and 0.06 time constants. One aspect of the present invention is that it calculates VFRs for small and large time constants, including time constants at least as small as those encountered during cardiac heartbeat cycles in the aorta.

In this regard, the present invention uses changes between two or more velocity profiles that occur over one or more time intervals to calculate the value for dimensionless time and then uses the values of one or more instances of dimensionless time to calculate the parameters in f(D). Further in this regard, the present invention may use the parameters that characterize f(D) to calculate the cross-sectional area of the fluid channel. Still further in this regard, the present invention may use one or more calculated cross-sectional areas of the fluid channel in conjunction with one or more velocity profiles to calculate one or more VFRs.

The following derivation and example use a circular tube as the channel. It should be noted, however, that the present invention is not limited to this geometry. Unsteady laminar flow in a circular tube is the starting point for the mathematical derivation. In this regard, a pressure gradient exists along the tube's length, that causes the fluid to accelerate until it reaches steady state velocity. Cylindrical coordinates may be used along with the following variables:

$\mu$=fluid viscosity
$\rho$=fluid density
L=tube length
R=tube radius
t=time
p=pressure. Note that $$\frac{p_0 - p_L}{L}$$

is the pressure gradient along the tube.
v, $v_z$=velocity along the length of the tube
$V_{max}$=maximum velocity of fluid at time t=∞. $V_{max}$ will occur at r=0 and $$V_{max} = \frac{(p_0 - p_L)R^2}{4\mu L} \text{ is the maximum velocity at } t = \infty.$$

Equations 1-3 define dimensionless variables for velocity, radius, and time respectively. In this regard, equation 1 defines dimensionless velocity, which is the actual velocity divided by the maximum velocity that would occur at time t=∞, equation 2 defines the dimensionless radius, and equation 3 defines the dimensionless time.

$$\phi = 4\frac{v_z \mu L}{(p_0 - p_L)R^2} \quad (1)$$

$$\xi = \frac{r}{R} \quad (2)$$

$$\tau = \frac{\mu t}{\rho R^2} \quad (3)$$

Equation 3 can be solved for the radius, R:

$$R = \sqrt{\frac{\mu t}{\tau \rho}} \quad (4)$$

From reference 1 [R. Byron Bird, Warren E. Stewart, and Edwin N. Lightfoot *Transport Phenomena*, John Wiley & Sons, Inc. (1960), pages 127-130], which is incorporated herein by reference, the following relationship related to force balance in a fluid channel is known:

$$\rho\left(\frac{\partial}{\partial t}v_z\right) = \frac{p_0 - p_L}{L} + \frac{\mu\left(\frac{\partial}{\partial r}r\left(\frac{\partial}{\partial r}v_z\right)\right)}{r} \quad (5)$$

The initial and boundary conditions are as follows:

The initial conditions for the start up case from zero velocity are: at t=0 the fluid will have $v_z$=0 for 0≤r and for r≤R, where R=Radius of circular tube.

The first boundary condition is that at r=0 the fluid will have $v_z$=finite value.

The second boundary condition is that at r=R the fluid will have $v_z$=0.

Equation 5 may then be multiplied by $$\frac{4L}{p_0 - p_L},$$

and after substituting in dimensionless velocity, radius, and time becomes:

$$\frac{\partial}{\partial \tau}\phi = 4 + \frac{\frac{\partial}{\partial \xi}\xi\left(\frac{\partial}{\partial \xi}\phi\right)}{\xi} \quad (6)$$

Equation 6 may be solved so that the following conditions are met:

The initial condition for the case where there is a zero velocity: at τ=0; φ=0

The first boundary condition: at ξ=1; φ=0

The second boundary condition: at ξ=0; φ=finite value.

The steady state will occur when τ=∞. Therefore, the solution is the sum of a steady state term and a transient term:

$$\phi(\xi,\tau)=\phi_\infty(\xi)-\phi_t(\xi,\tau) \quad (7)$$

Steady state occurs at τ=∞ and at steady state $$\frac{\partial}{\partial \tau}\phi = 0.$$

Substituting this value into Equation (6) and solving at φ=0 and ξ=1 leads to equation 8:

$$\phi_\infty(\xi)=1-\xi^2 \quad (8)$$

Reference 1 derives the following expression related to development of the velocity profile equation:

$$\phi_1(\xi,\tau) = \sum_{n=1}^{\infty} B_n e^{(-\alpha(0,n)^2 \tau)} J(0, \alpha(0,n)\xi) \quad (9)$$

where J(n, x) is the n-th order Bessel function of the first kind and α(0,n) is the n-th positive real root of the zeroth order Bessel function of the first kind.

The initial condition occurs when τ=0 so $$\phi(\xi, 0) = 1 - \xi^2 - \left(\sum_{n=1}^{\infty} J(0, \alpha(0,n)\xi) B_n\right) \quad (10)$$

So far, the derivation does not depend on the initial velocity distribution. The standard development of the velocity flow profile equation would now assume that the initial velocity is zero. Such an assumption significantly simplifies the mathematics, but it also fails to generate equations that can be used to determine the dimensions of the channel. The remainder of the derivation presented departs from the standard development of the velocity flow profile equation.

In this regard, the initial velocity distribution can be represented by a generalized equation. Various forms of such generalized equations may be used. When the pressure gradient does not reverse direction (although the magnitude in a single direction can change) an equation of the following form correctly represents all of the possible initial velocity distributions:

$$\phi=a(1-\xi^k) \quad (11)$$

where a=maximum φ that occurs for the measured velocity profile.

If the initial velocity is zero then a=0. When the flow rate is increasing from a non-zero initial velocity then a<1. If the velocity is decreasing then a>1. If a>1 then the pressure gradient is decreasing. This same functional form can be used with dimensioned velocity. In that case a=the maximum velocity that occurs for the measured velocity profile and k=the velocity profile shape parameter. k is defined on the closed interval [2,∞]. For fully developed laminar flow the profile is parabolic and k=2. For less than fully developed profiles k>2.

Substituting equation (11) for φ(ξ,0) in equation (10) produces equation (12):

$$a(1-\xi^k) = 1 - \xi^2 - \left(\sum_{n=1}^{\infty} J(0, \alpha(0,n)\xi) B_n\right) \quad (12)$$

Equation (12) may then be solved for $B_n$ by multiplying by $J(0, \alpha(0, m)\xi)\xi$ and then integrating. The result is equation 13.

$$\int_0^1 J(0, \alpha(0, m)\xi)\xi a - J(0, \alpha(0, m)\xi)\xi a\xi^k d\xi = \quad (13)$$

$$\int_0^1 J(0, \alpha(0, m)\xi)\xi d\xi + \int_0^1 -J(0, \alpha(0, m)\xi)\xi^3 d\xi +$$

$$\left(\sum_{n=1}^\infty B_n \int_0^1 -J(0, \alpha(0, m)\xi)\xi J(0, \alpha(0, n)\xi) d\xi\right)$$

The orthogonality properties of Bessel functions lead to contributions only when m=n. Therefore, the sum can be eliminated. Solving for $B_m$ leads to equation (14).

$$B_m = -2\frac{a\alpha(0, m)^2 - a\alpha(0, m)^{(2-k)} \text{LommelS1}(1+k, 0, \alpha(0, m)) - 4}{J(1, \alpha(0, m))\alpha(0, m)^3} \quad (14)$$

where LonunelS1 is the Lommel function s.

For the case where the initial condition has a non-zero velocity the resulting equation for $\phi(\xi,\tau)$ including the variables that characterize the initial velocity conditions, is $$\phi(\xi, \tau, a, k) = \quad (15)$$

$$1 - \xi^2 - \left(\sum_{n=1}^\infty \left(-2\frac{\begin{array}{c}(a\alpha(0, n)^2 - a\alpha(0, n)^{(2-k)} \text{LommelS1}(1+\\ k, 0, \alpha(0, n)) - 4)e^{(-\alpha(0,n)^2\tau)}J(0, \alpha(0, n)\xi)\end{array}}{J(1, \alpha(0, n))\alpha(0, n)^3}\right)\right)$$

The velocity distribution is described by equation 11. At any particular time when a velocity profile is measured it will have values $\alpha_t$, $k_t$ leading to equation (16).

$$\phi(t) = a_t(1 - \xi^{k_t}) \quad (16)$$

The dimensionless time, $\tau$, is a function of time. The velocity distribution starts developing from an initial velocity profile, which is characterized by equation (11) where a and k are the parameters that characterize the shape of the initial velocity distribution. The result is EQ. 17:

$$a_t(1 - \xi^{k_t}) = \quad (17)$$

$$1 - \xi^2 - \left(\sum_{n=1}^\infty \left(-2\frac{\begin{array}{c}(a\alpha(0, n)^2 - a\alpha(0, n)^{(2-k)} LommelS1\\ (1+k, 0, \alpha(0, n)) - 4)e^{-\alpha(0,n)^2\tau}\\ J(0, \alpha, (0, n)\xi)\end{array}}{J(1, \alpha(0, n))\alpha(0, n)^3}\right)\right)$$

The summation from n=1 to $\infty$ can be approximated by summing to N, as shown in equation 18.

$$a_t(1 - \xi^{k_t}) = \quad (18)$$

$$1 - \xi^2 - \left(\sum_{n=1}^N \left(-2\frac{\begin{array}{c}(a\alpha(0, n)^2 - a\alpha(0, n)^{(2-k)} LommelS1\\ (1+k, 0, \alpha(0, n)) - 4)e^{-\alpha(0,n)^2\tau}\\ J(0, \alpha, (0, n)\xi)\end{array}}{J(1, \alpha(0, n))\alpha(0, n)^3}\right)\right)$$

The flow profile depends upon four variables. Two of the variables, a and k, define the initial velocity profile. A third variable, $\tau$, characterizes the elapsed time. The fourth variable, $\xi$, characterizes the radius of the tube.

In this regard, the present invention uses data from velocity measurements to evaluate velocity profile parameters and then determines the values of other variables, such as channel dimensions based upon changes that occur in velocity profile parameters during a known time interval. The following method is an example of using changes in velocity profiles to determine channel dimensions and then to calculate VFRs and derived parameters. The general steps taken to calculate channel dimensions and VFRs using the above described formulas are as follows:

(1) at a specific time, make velocity measurements using a suitable means, such as by using an interrogating signal such as a beam of ultrasonic or electromagnetic waves, and create a velocity profile. As is well known, range information associated with received signals can be determined based on signal transit time and signal speeds in the medium. Accordingly, velocity measurements for fluid particles as well as the locations of those particles can be determined to obtain profile related information.

(2) use the velocity profile to calculate the values for parameters that characterize a velocity profile function. Examples of such parameters are a and k in equation (11) and equation (11) is an example of a function that characterizes velocity profiles. As described in detail later, such calculations may use only two data points or the calculations may use more than two data points in conjunction with statistical curve fitting techniques such as least squares or least absolute value methods.

(3) after a known time interval, t (measured in, for example, seconds), has elapsed make more velocity measurements and calculate values for the parameters that characterize the velocity profile at time t. For example, using equation 11, a and k for this second profile can be designated as $a_t$, $k_t$. In particular, the velocity profile change can be analyzed over a time period that is sufficiently short that changes in flow parameters such as channel dimension and pressure gradient can be safely assumed to be negligible. Such parameters vary with the patient's pulse cycle which will generally have a frequency between 0.5-4.0 Hz. Accordingly, the time interval within which changes in velocity profile parameters are analyzed is preferably no longer than about 0.025 seconds and, more preferably, no more than about 0.01 seconds. It will be appreciated, however, that the time interval(s) may alternatively be phase synchronized relative to the patient's pulse cycle or changes in flow parameters may be taken into account.

(4) calculate dimensionless time, $\tau$, using a functional relationship that characterizes how velocity profiles change with time. For example, use equation (17) or (18) and the values for a, k, $a_t$, $k_t$, to calculate $\tau$.

(5) use an equation that relates dimensionless time to channel dimensions to calculate the channel's dimensions. For example, use equation (4), along with the known the values for t, viscosity, and density (or the kinematic viscosity, which is the quotient of viscosity and density) to calculate the tube's radius, R.

(6) use the now known channel dimensions to calculate the channel's cross-sectional area, A. For example, use the radius, R, to calculate the cross-sectional area.

(7) use the measured velocity profile to calculate the mean velocity $v_m$. For example, as described later, the mean value of a velocity profile defined by equation 11 across a tube with circular cross-section is $$v_{mean} = \frac{ka}{2+k}$$

where a is the maximum dimensioned velocity that occurs at the time of measurement. As described below, the parameters for the velocity profile function, in this case a and k, can be solved for directly so that they are readily available for use in calculating mean velocities.

(8) calculate the VFR=A×$v_m$ (9) use a relationship that defines dimensionless velocity to calculate the pressure gradient. For example, use a rearranged form of equation (1) to calculate the pressure gradient.

(10) calculate the radius and pressure gradient at two different times and divide the change in radius by the change in pressure gradient to calculate a channel elasticity.

As noted above, when the initial velocity profile is zero then a=0 in equation (15). At steady state (τ=∞) the fully developed laminar flow profile is parabolic, as depicted in FIG. 1. The highest velocity is at the center of the tube and v=0 at the wall of the tube.

Figure 2:
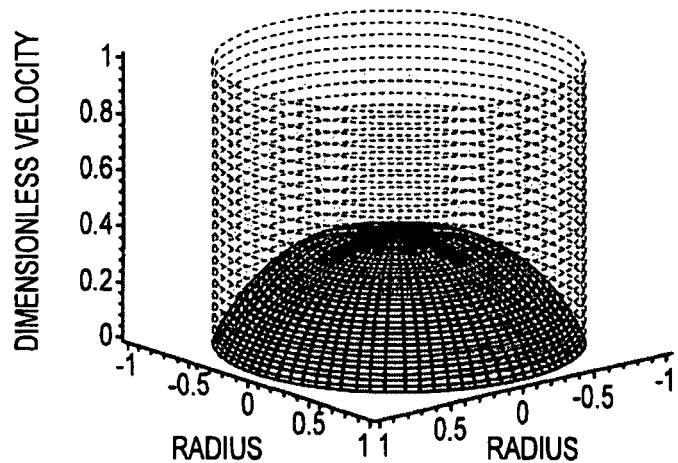
FIG. 2 illustrates dimensionless velocity profile for developing laminar flow.
Figure 3:
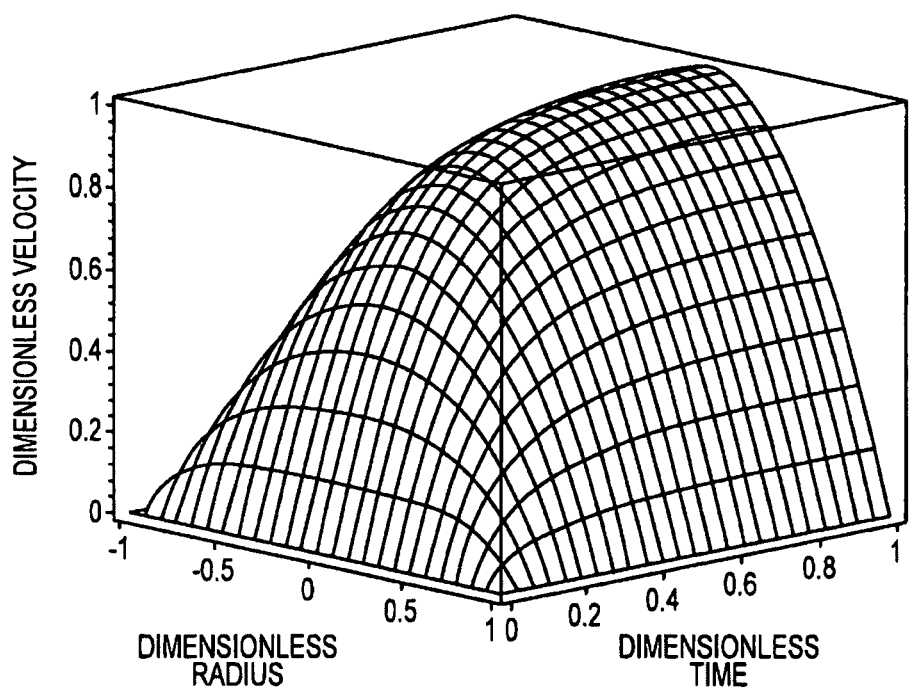
FIG. 3 illustrates changes in velocity profiles after startup from zero velocity.
Figure 4:
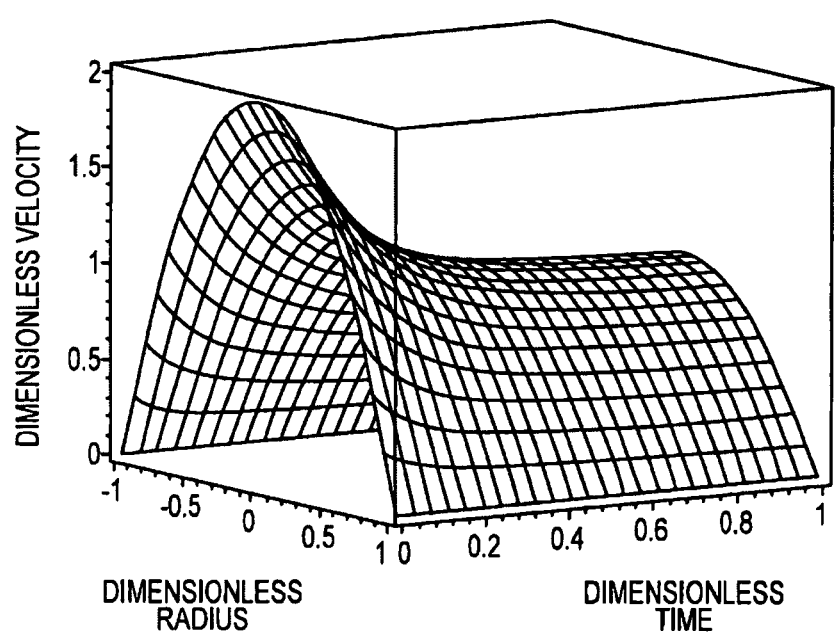
FIG. 4 illustrates changes in velocity profiles after startup from non-zero velocity larger than that which will occur at steady state.

As flow is developing the velocity profile is blunter, as depicted in FIG. 2. FIG. 2 represents the situation that arises when the initial velocity is zero and when enough time has elapsed for τ=0.1. FIG. 3 depicts the velocity profiles as they change from τ=0 to τ=1. When τ=1 the velocity profile is almost fully developed. FIG. 4 depicts the situation where the velocity is decelerating because the pressure gradient is decreasing.

All of the flow profiles depicted for the cases shown in FIGS. 1-4 are accurately represented by equation (11). This functional form is the limit of equation (18) as N approaches ∞.

Figure 5:
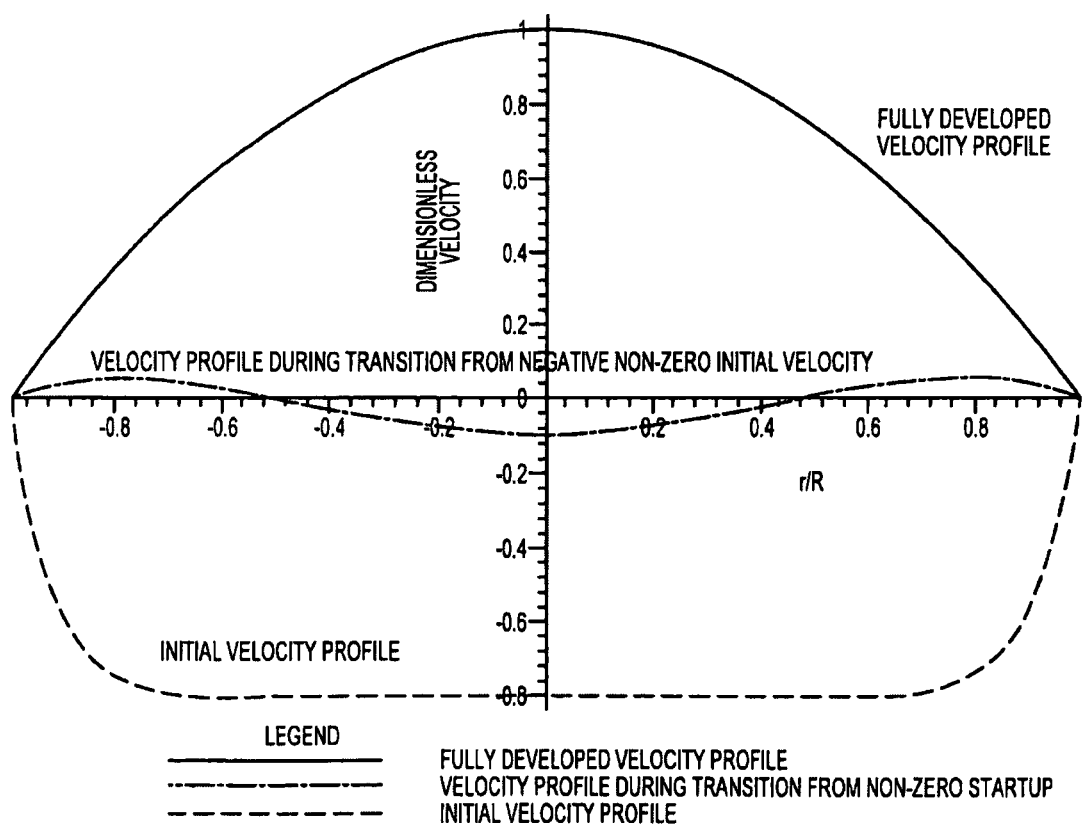
FIG. 5 illustrates changes in velocity profiles when the pressure gradient reverses direction.

FIG. 5 depicts the case where the pressure gradient has reversed directions. In FIG. 5, the dimensionless radius is on the axis labeled as r/R. FIG. 5 also illustrates a starting non-negative velocity profile at the bottom of the figure and a final steady state velocity profile at the top of the figure. Both of these profiles conform to the function form of equation (11). The curved middle velocity profile in FIG. 5 depicts a transitional velocity profile as the flow field reverses direction between the initial velocity profile and the final profile. The transition has the fluid in the center of the tube flowing down while the fluid at the edges has reversed and is flowing up. Such a case could occur, for example, if the aortic valve suffers significant backflow. A more complicated expression for the initial velocity profile is needed for cases where the pressure gradient reverses direction and will include more than the two parameters used in equation (11).

Figure 6:
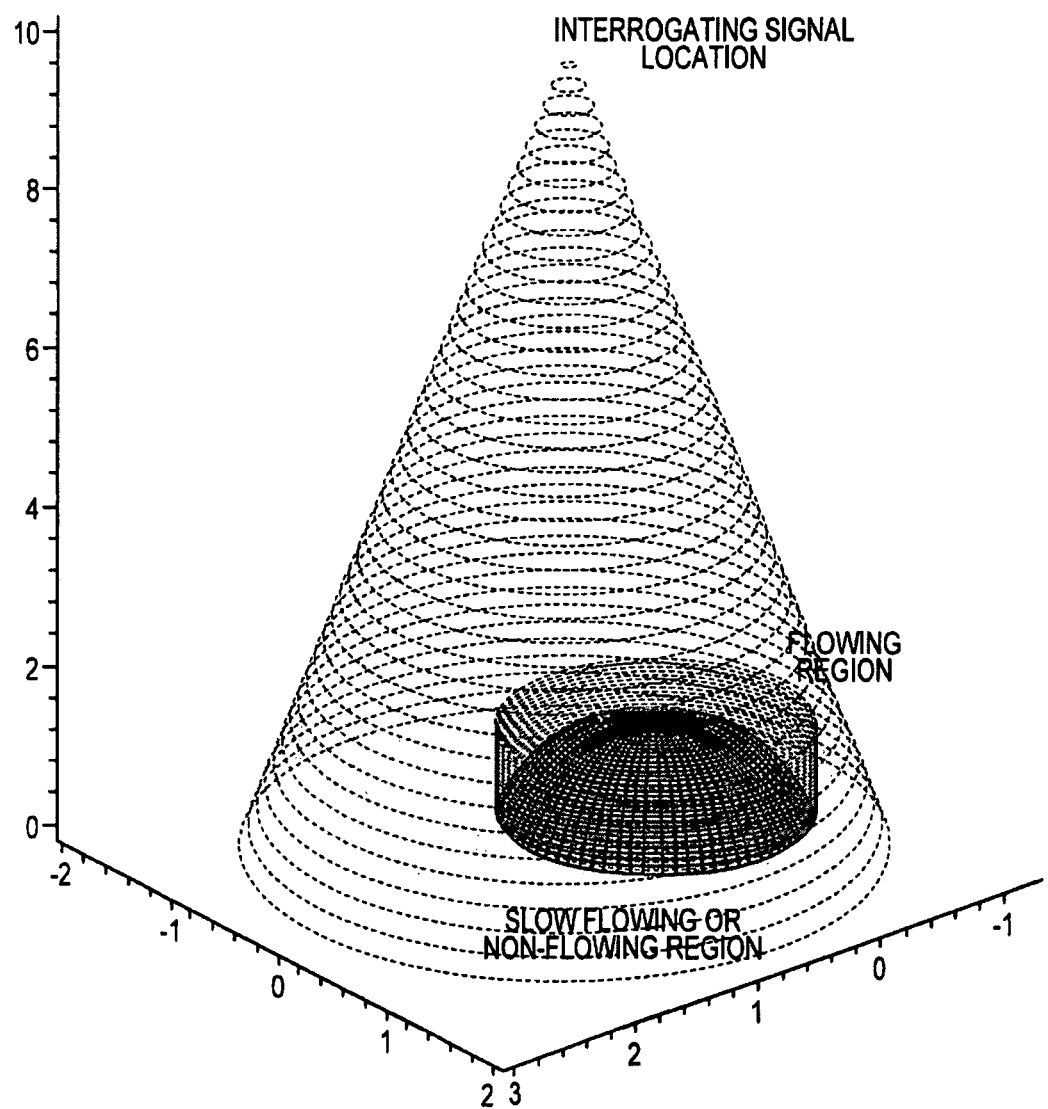
FIG. 6 illustrates an interrogating signal and the regions producing measured signal.

As noted above, another aspect of the present invention is adjusting for sources of errors. Errors may exist in the measured velocity profiles, particularly when an interrogating signal is used to produce the measured data. FIG. 6 schematically portrays a case where an interrogating signal, such as ultrasound, is being beamed into a region containing a flowing fluid contained in a tube that is surrounded by a region of materials that are moving substantially more slowly (either in the same or opposite direction as the flowing fluid) than most of the material flowing in the tube. The slow moving material is essentially stationary compared to the flowing fluid. For illustrative purposes, only a portion of the tube containing fluid is shown in FIG. 6.

The situation portrayed in FIG. 6 is similar to that which would occur if an ultrasonic Doppler measurement were made of the blood flowing in the ascending aorta and the Doppler transducer is located in the suprasternal notch and aimed toward the heart. Some of the interrogating signal is echoed or backscattered, which is not depicted in FIG. 6, and can be measured as a return signal. The frequency spectrum of the returned signal can be analyzed to produce estimates of the velocity profile of the region interrogated.

In this case, two sources of error exist. A first source of error may be present in signals measured from the flowing region that add errors such as noise. A second source of error may be present from signals representing the slow moving material region that confound signals from the flowing region, so that slow moving velocity signals are added to the velocity signals from the flowing fluid. According to the present invention, these two sources of errors are accounted for and prevented from producing significant errors in the estimated VFRs. The general solution is to absorb the errors by introducing mathematical structures that selectively pick these errors from the measured signal. The following is a derivation of a general and a specific example of error absorbing functions that may used to estimate distributions of measured signals or variables derived from measured signals. An example of a measured signal is the frequency from a Doppler measurement. Derived variables are variables calculated using one or more measured signals, such as velocities calculated from Doppler frequency measurements.

The general form of a general error absorption function that can be used to determine channel dimensions and VFRs is given by equation (19) as follows:

$$M(f)=S(f,|x_s|)+F(f,|x_F|) \quad (19)$$

where
M(f)=the measured signal
$S(f,|x_s|)$=the signal from the slow moving region, where $|x_s|$ are a vector of parameters (to be determined) that characterize the slow moving region.
$F(f,|x_F|)$=the signal from flowing region, where $|x_F|$ are a vector of parameters (to be determined) that characterize the errors, such as noise.

Figure 7:
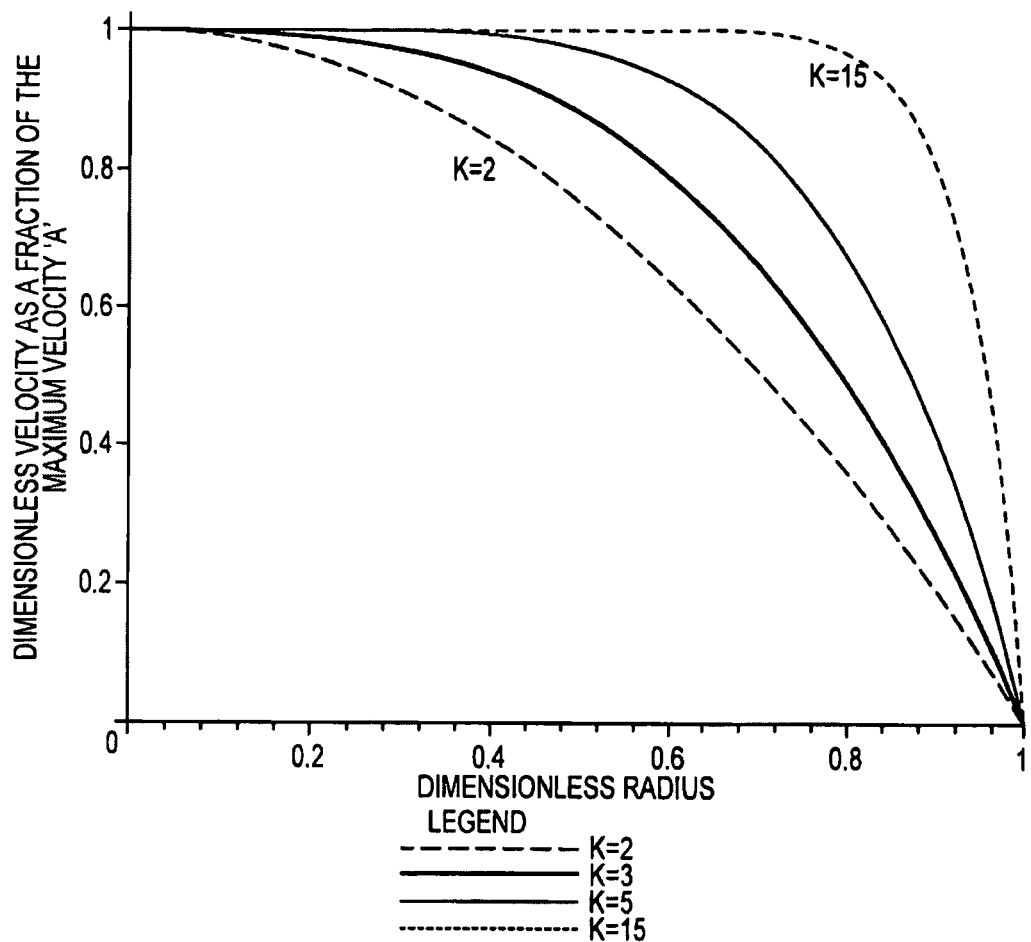
FIG. 7 illustrates example dimensionless velocity profiles.

FIG. 7 illustrates velocity profiles of fluids moving in channels as calculated using equation (11) with a=1. Any particular value of dimensionless radius, ξ*, maps to one and only one dimensionless velocity, φ*. For a tube, each dimensionless radius forms a circle around the center of the tube. All of the fluid moving through the tube at a particular ξ* will move with the same velocity φ*. Any randomly selected fluid element will have a 100% likelihood of being in an area that is between the center of the tube and the outermost radius, where ξ=1. The probability of the fluid element being in a band extending from the outermost radius and inner radius is the ratio of the total cross-sectional area of the tube and the radius of the band of on the interval [ξ,1]. Thus, $$F(\xi) = \frac{\pi - \pi\xi^2}{\pi},$$

which simplifies to equation 20:

$$F(\xi)=1-\xi^2 \quad (20)$$

This result can be interpreted as the probability that a random fluid element will be in a band between radius ξ and the outer radius (where ξ=1) of the tube. For example, the probability that a random ξ will be in the ring with a radius between ξ=0.9 and ξ=1 is 0.19. In other words, 19% of the area of a circle lies outside of radius ξ=0.9.

A related problem is solving for the value of ξ beyond which a selected fraction of the area resides. In this case, equation (21) can be used to show that the radius beyond which 19% of the area lies is ξ=0.9.

$$\xi=\sqrt{-F+1} \quad (21)$$

Figure 8:
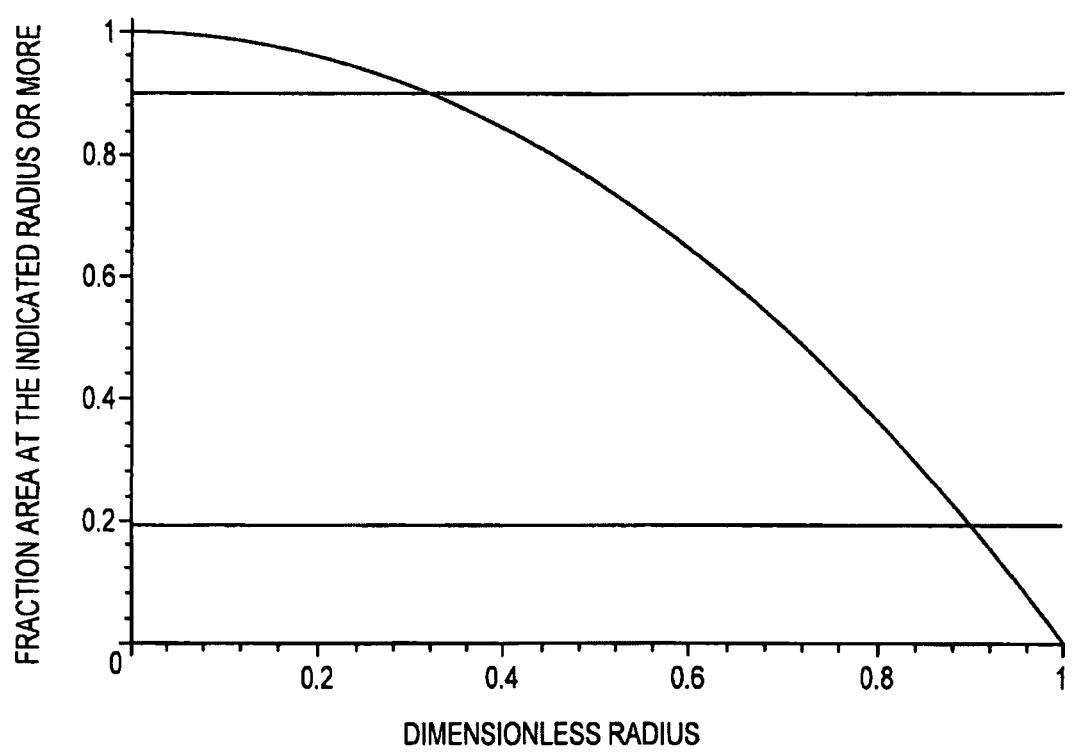
FIG. 8 graphs the cumulative probability distribution of the area of a circle.

Calculating the radius beyond which 90% of the area lies gives ξ=0.3162. Equation (21) can be interpreted as a cumulative probability distribution as illustrated in FIG. 8. FIG. 8 illustrates, for example, that 100% of the area is at a radius of over 0 and that none of the area is beyond a radius of 1. Also, FIG. 8 illustrates that 19% of the area lies outside of ξ=0.9 and that 90% of the area lies in the region bounded by ξ=0.3162 and ξ=1.

The relationship between dimensionless velocity and dimensionless radius, equation (11), ϕ=a (1−ξ$^k$), shows that ϕ gets larger as ξ gets smaller. Therefore, substituting equation (21) into equation (11) leads to equation (22) or the maximum dimensionless velocity that occurs when an annular ring extends between ξ and 1.

$$\phi = -a(-1 + (-F+1)^{(1/2k)}) \qquad (22)$$

Figure 9:
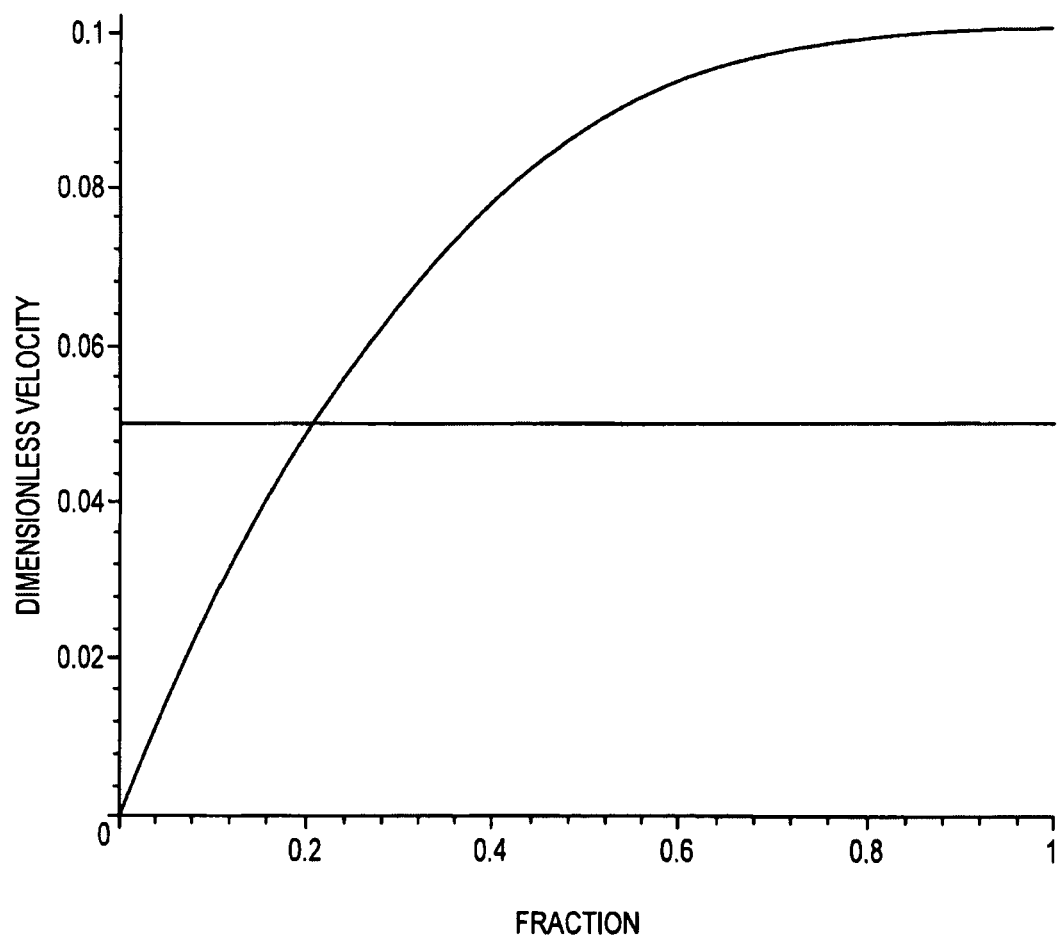
FIG. 9 illustrates how dimensionless velocity ($\phi$) changes with the fraction of cross-sectional area.

For example, the maximum dimensionless velocity that occurs when a=0.1, k=6, and F=0.5 is ϕ=0.0875. Equation 22 can be plotted, as illustrated in FIG. 9, which illustrates how ϕ changes as the fraction F varies. It should be noted that FIG. 9 is calculated using a=0.1 and k=6.

The maximum range of ϕ is the interval [0,a]. The variable a is the maximum value of the dimensionless velocity that occurred at the time that a velocity profile was measured.

Figure 10:
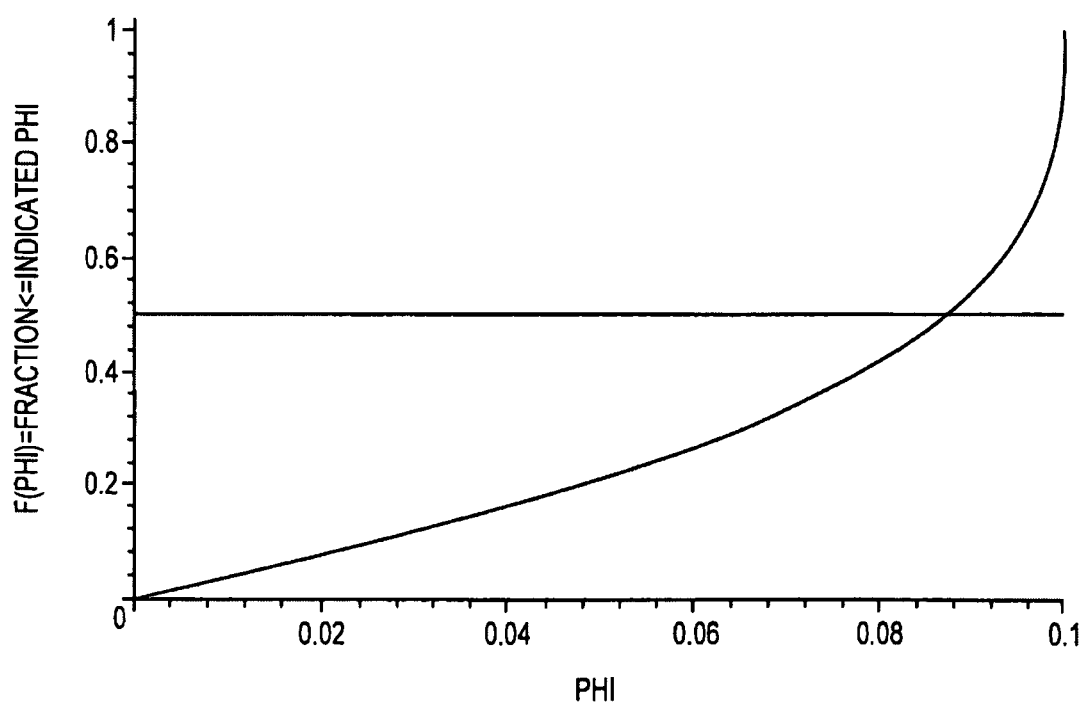
FIG. 10 graphs an example cumulative probability function for dimensionless velocity for developing laminar flow.
Figure 11:
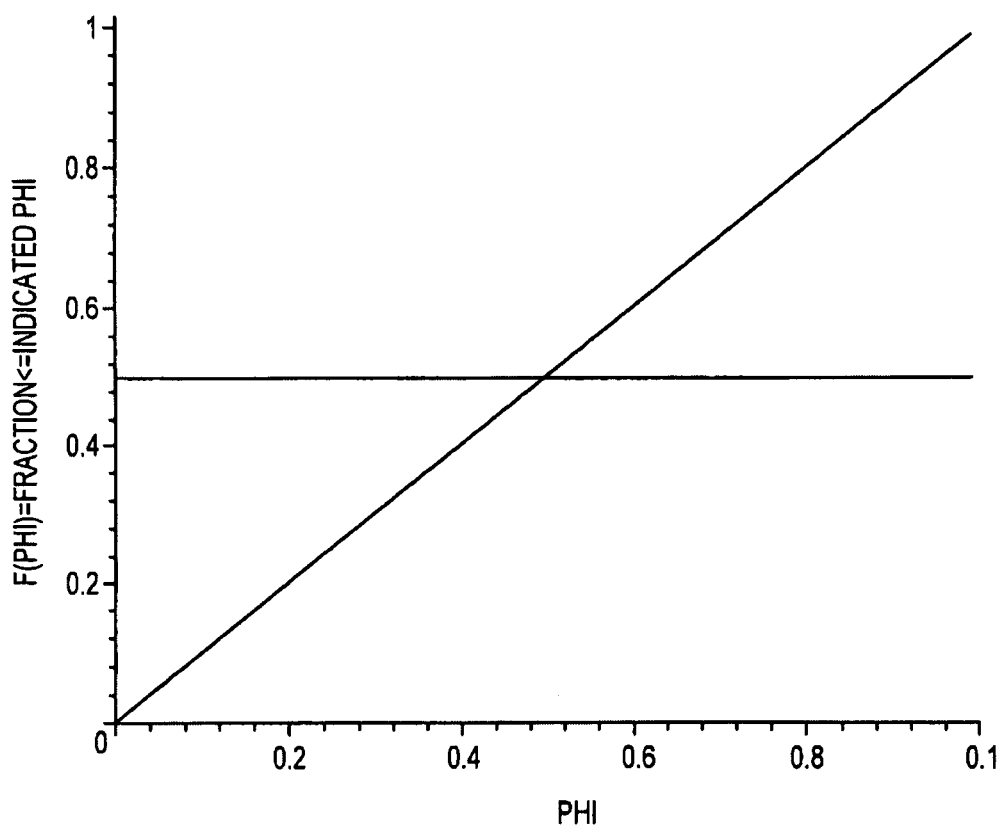
FIG. 11 graphs an example cumulative probability function for dimensionless velocity for fully developed laminar flow.

The fraction, F, in equation (22) can be interpreted as a probability and solved for the more traditional equation (23) representing the cumulative distribution of ϕ that gives the fraction of the dimensionless velocities that are less than or equal to a particular ϕ.

$$F(\phi) = -\left(-\frac{\phi - a}{a}\right)^{\left(2\frac{1}{k}\right)} + 1 \qquad (23)$$

ϕ has a domain on the closed interval [0, a], where a is the maximum dimensionless velocity that occurred at the time of a particular measurement. Therefore, the cumulative function is only defined for ϕ on the interval [0,a]. For example, if a=0.1 and k=6, a plot over the maximum range that ϕ can have results in FIG. 10. FIG. 10 illustrates that when a=0.1 and k=6, 50% of the dimensionless velocities are less than or equal to ϕ=0.0875. For fully developed laminar flow a=1 and k=2, the corresponding cumulative distribution has ϕ defined between 0 and 1, as illustrated in FIG. 11. The corresponding equation is therefore, $F_{fully\_developed\_laminar\_flow}(\phi) = \phi$ and for a fully developed laminar flow the probability of having any particular dimensionless velocity is linear.

The mean value of a parameterized velocity profile can be found by using equation (24).

$$\phi_{mean} = \frac{ka}{2+k} \qquad (24)$$

If dimensioned velocity is used to solve for a and k then the value of k will be the same as when dimensionless velocity is used in the calculation and a will become the dimensioned value for the largest velocity in the measured velocity profile. The mean dimensioned velocity can then be calculated using equation (25).

$$v_{mean} = \frac{ka}{2+k} \qquad (25)$$

Equation (23) is the cumulative probability function. The probability density function for ϕ is found by taking the derivative of the cumulative probability function. The result is given in equation (26). As before, ϕ exists on the interval [0, a]. When fully developed laminar flow (k=2, a=1) exists, the result will be f(ϕ)=1. For developing laminar flow (including that which occurs when the pressure gradient decreases) k>2 so the probability density function for developing laminar flow will always have a positive exponent that is less than 1.

$$f(\phi) = 2\frac{\left(-\frac{\phi}{a} + 1\right)^{\left(2\frac{1}{k} - 1\right)}}{ka} \qquad (26)$$

Measurement errors alter the probability that the measured ϕ is the correct value for ϕ. The probability of having a particular $\phi_n$ occur and of having the noise added to it leading to a total value less than or equal to ϕ is the product of the probability that will have $\phi_n$ times the probability that will have $\phi_n$+noise≤ϕ, which can be represented as p(ϕ) p($\phi_n$+noise≤ϕ). The product of these two probabilities is the cumulative probability that will have a total measured value $\phi_n$≤ϕ.

The probability of having a particular $\phi_n$ is the product of the density function evaluated at $\phi_n$dϕ. Let p($\phi_n$) denote the probability of ϕ taking on the specific value $\phi_n$. In general, the noise will have a distribution associated with it that is defined by a vector of parameters, H. For a Gaussian distribution, the parameters are the mean and standard deviation. Let the probability density function for the noise generating function be $g_{noise}(\phi, H)$. The probability of having a particular $\phi_n$ and the noise centered around it being less than or equal to a velocity is the product of two probabilities: (probability of a particular $\phi_n$)×(probability of x+$\phi_n$≤ϕ) for a particular $\phi_n$. The result is the joint probability given in equation (27):

$$p(\phi_n, x + \phi_n \le \phi) = p(\phi_n) \int_{-\infty}^{\phi} g_{noise}(x, H) dx \qquad (27)$$

The cumulative probability is the probability that will have (x+$\phi_n$≤ϕ) for all $\phi_n$ is the sum of the individual probabilities for all $\phi_n$, which is the same as integrating over all $\phi_n$. Taking equation (26) as p($\phi_n$) and setting up the integral so that $\phi_n$ is over the interval [0,a] (because the maximum value for ϕ is a) leads to equation (28) which forms the general case:

$$F_{noise}(\phi) = \int_0^a 2\frac{\left(-\frac{\phi_n}{a} + 1\right)^{\left(2\frac{1}{k} - 1\right)} \int_{-\infty}^{\phi} g_{noise}(x, H) dx}{ka} d\phi_n \qquad (28)$$

A case of particular interest is when the noise is a Gaussian (normal) distribution. When it is reasonable to assume that many independent factors contribute to the measurement error and that these factors produce additive effects, then the Central Limit Theorem states that the errors will have a Gaussian distribution about the true value. Therefore, the noise density function is centered about $\phi_n$, and $\phi_n$ is the mean, and the noise function has a standard deviation σ:

$$g_{noise}(\phi_n) = \frac{1}{2}\frac{\sqrt{2} e^{\left(-1/2 \frac{(x-\phi_n)^2}{\sigma^2}\right)}}{\sigma\sqrt{\pi}} \qquad (29)$$

Combining this equation with equation (27) gives the joint probability:

$$p(\phi_n, x + \phi_n \leq \phi) = p(\phi_n) \int_{-\infty}^{\phi} \frac{1}{2} \frac{\sqrt{2} \, e^{\left(-1/2 \frac{(x-\phi_n)^2}{\sigma^2}\right)}}{\sigma \sqrt{\pi}} dx \quad (30)$$

The cumulative probability is the probability that will have $(x+\phi_n \leq \phi)$ for all $\phi_n$ is the sum of the individual probabilities for all $\phi_n$, which is the same as integrating over all $\phi_n$. Substituting and integrating by $\phi_n$ over the interval [0,a] (because the maximum value for $\phi$ is a) leads to equation (31):

$$F_{noise}(\phi) = \int_0^a 2 \frac{\left(-\frac{\phi_n}{a}+1\right)^{\left(2\frac{1}{k}-1\right)} \int_{-\infty}^{\phi} \frac{1}{2} \frac{\sqrt{2} \, e^{\left(-1/2 \frac{(x-\phi_n)^2}{\sigma^2}\right)}}{\sigma \sqrt{\pi}} dx}{ka} d\phi_n \quad (31)$$

Upon evaluation and substituting x for $\phi_n$, equation (31) becomes an equation that explicitly incorporates the distribution of $\phi$ for the actual velocity distribution and random noise that alters that actual values and produces the measured distribution, resulting in equation (32):

$$F_{noise}(\phi) = \int_0^a 2 \frac{\left(-\frac{x}{a}+1\right)^{\left(2\frac{1}{k}-1\right)}\left(-\frac{1}{2}\mathrm{erf}\left(\frac{1}{2}\frac{\sqrt{2}(-\phi+x)}{\sigma}\right)+\frac{1}{2}\right)}{ka} dx \quad (32)$$

Figure 12:
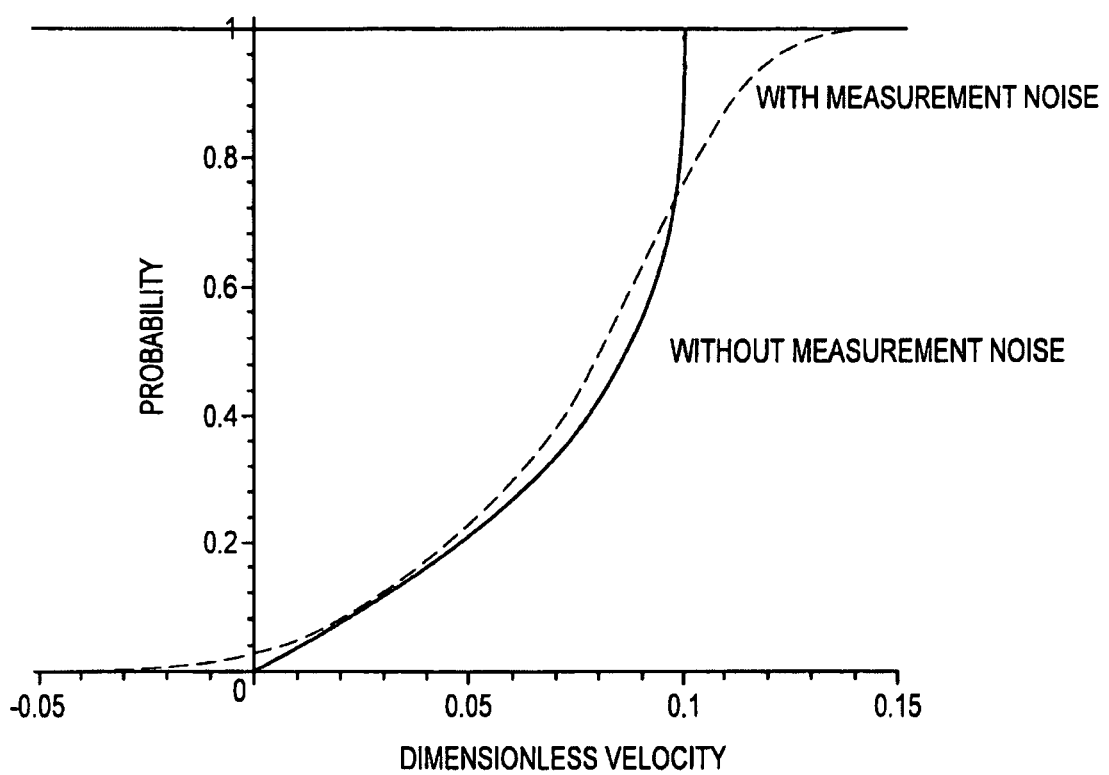
FIG. 12 graphs example cumulative probability functions without noise and with noise.

In this case, the noiseless $\phi$ is on the interval [0, a], while the measured $\phi$ (including noise) can extend beyond the interval [0, a]. FIG. 12 illustrates how Gaussian distributed random errors in the dimensionless velocity, $\phi$, affect the cumulative distribution. The errors spread the possible values for measured velocities so that they are both smaller and larger than the actual values that occur in the flowing fluid.

Equation 28 is the general form of the cumulative spectral function with an error absorption function used to compensate for errors in the measured signal. Equation (32) is the specific case when the measurement error function is Gaussian. Other functional forms may be used instead of Gaussian, such as exponential, Cauchy, and Riceian.

The probability density function that corresponds to equation 32 is therefore:

$$f_{noise}(\phi) = \int_0^a \frac{\left(-\frac{x}{a}+1\right)^{\left(2\frac{1}{k}-1\right)} e^{\left(-1/2 \frac{(-\phi+x)^2}{\sigma^2}\right)} \sqrt{2}}{ka\sqrt{\pi}\,\sigma} dx \quad (33)$$

Figure 13:
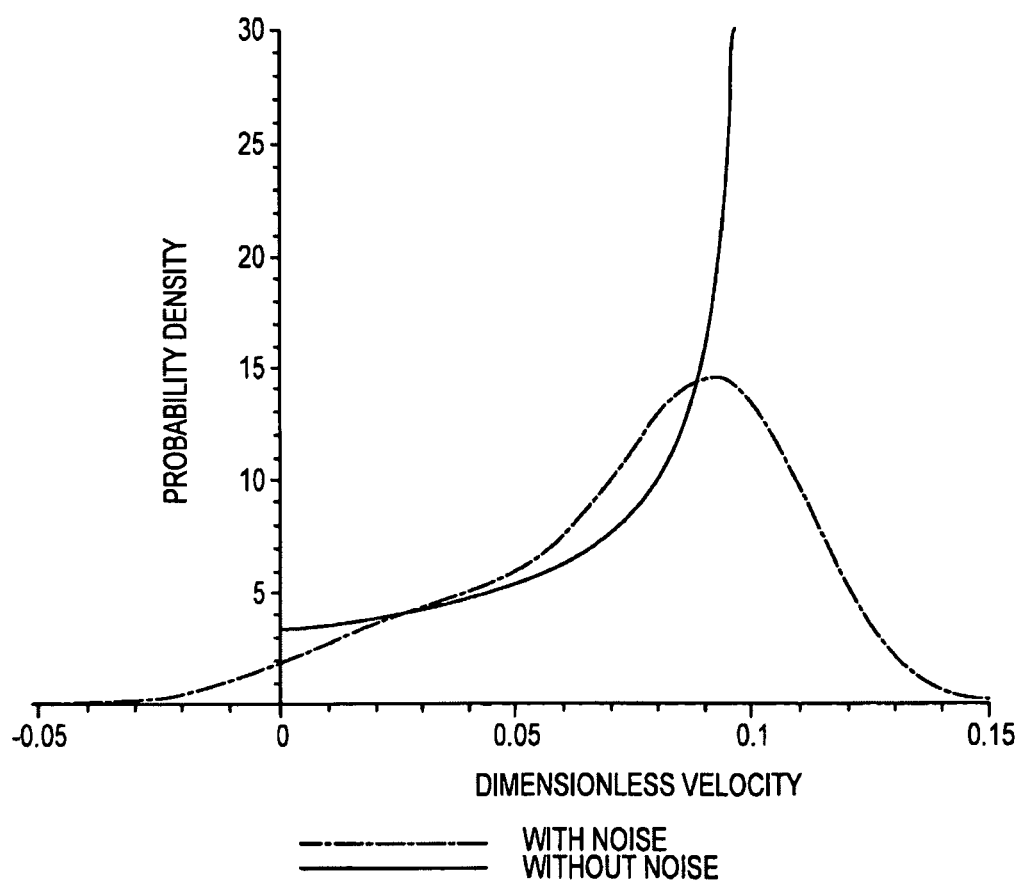
FIG. 13 graphs example probability density functions without noise and with noise.

FIG. 13 illustrates how the probability density function is affected by the presence of Gaussian distributed random errors. It should be noted that the spreading of the probability density function, as exemplified in FIG. 13, is caused by the measurement errors. Using error absorption functions to reduce or remove such errors, including those caused by random fluctuations that are commonly referred to as "noise", is a general technique that is employed as part of the novel art of the current invention. It should be noted, however, that using error absorption functions to reduce or remove such errors according to the present method is particularly advantageous for determining velocity profiles (either dimensionless or with dimensions) and the subsequent calculations that lead to determining VFRs.

The probability density functions are the spectral density functions that are produced by the frequency shifts produced by Doppler measurement methods. When measurement noise is introduced, the parameters that characterize the error absorption function $g_{noise}(\phi,H)$ can be solved for, as well as for values of a and k that characterize the shape of the velocity profile. For example, if the noise absorption function is Gaussian then the value for standard deviation is solved for to characterize the noise absorption function.

As discussed above, FIG. 9 illustrates an interrogating signal being used as part of a system to determine the velocity profile as part of the process of determining the VFR of the flowing region. In this regard, the above error absorption functions can be used to reduce or remove measurement errors in the signals from the flowing region. However, the other source of possible error is the confounding signals that come from the slow flowing or non-flowing materials that are outside of the flowing region also shown in FIG. 9. In this regard, errors that may be caused by signals from slow moving and non-flowing materials may also be reducing or removed as follows.

The general form for the cumulative probability distribution is:

$$F(\phi) = F_{slow}(\phi) + F_{flowing}(\phi) \quad (34)$$

As will be further described below, $F_{flowing}(\phi)$ represents the flowing material's distribution as expressed for example by equation 32, after it has been adjusted for the fraction of the region producing signals that have flow $F_{slow}(\phi)$ represents the material that is non-flowing (either not moving or slow moving). $F_{slow}(\phi)$ will be represented by a distribution for the non-flowing velocities, which is generally Gaussian, often with a non-zero mean. It should be noted, however, that the distribution most suitable for a particular application may include exponential, Cauchy, Riceian, or other distributions. Absent other information to the contrary, however, a Gaussian distribution is an appropriate distribution to use as the velocities of the non-flowing region are assumed to be moving much slower than those of the flowing regions. Additionally, the velocities of the non-flowing materials will be produced by a multitude of independent time-varying parameters that all invoke the Central Limit Theorem.

By way of example, for the following derivation, a Gaussian distribution will be used as the error absorption function. It may be assumed that the slow moving velocities have a Gaussian distribution and that the mean may take on any value, including positive, negative, or zero at any instant when measurements are made. Additionally, the non-zero mean could occur, for example, if the measurement is of a region that includes the ascending aorta and the respiration processes occurring during the time of measurement causes a slow movement of the non-flowing region away from the location of the signal source. In this case, a fraction of the velocity signals will come from the flowing region and the balance will come from the slow moving region. The fraction of the signals from the two regions are used to weight the contributions from each region to the overall velocity distribution. For example, in the case where the interrogating signal is part of a Doppler system, the slow moving velocities produce Doppler echoes that are in addition to the echoes produced by the flowing velocities. They produce a total number of echoes at a particular velocity. In this regard, all of the echoes are added up and the total is used to normalize the number of counts at each velocity. In this regard, the number of counts from a particular region depend on its area, e.g. the number of counts that come from the slow moving region depend on its area, and the number of counts from the flow region depend on its area. The fractions of the total area for each region, which is all that matters in the probability distribution, define how much weight is given to the signals from the flowing region and from the slow moving region. In this regard, if $A_s$=area for the slow moving region and $A_f$=the area for the flow region the fraction for the slow moving region is $$f_s = \frac{A_s}{A_s + A_f}$$

and the fraction for the flow region is $$f_f = \frac{A_f}{A_s + A_f}.$$

The total fraction must equal 1 so $f_s+f_f=1$ must be true, which leads to $f_H=1-f_f$. These relationships lead to equation (35), which is the total cumulative probability for $\phi$ $$F_{noise,slow}(\phi) = (1-f_f)\int_{-\infty}^{\phi} \frac{1}{2}\frac{\sqrt{2}\,e^{\left(-1/2\frac{(\phi-\mu_s)^2}{\sigma_s^2}\right)}}{\sigma_s\sqrt{\pi}} d\phi + \tag{35}$$

$$f_f \int_0^a 2\frac{\left(1-\frac{x}{a}\right)^{\left(2\frac{1}{k}-1\right)}\left(\frac{1}{2}erf\left(\frac{1}{2}\frac{\sqrt{2}\,(\phi-x)}{\sigma}\right)+\frac{1}{2}\right)}{ka} dx$$

The total probability of having any particular $\phi$ or less is the sum of the two probabilities. The term on the left is the probability associated with the slow moving region and the term with the second term is the probability for the flowing velocities that have measurement noise represented by Gaussian noise.

In the case where the slow moving region is represented by a Gaussian distribution, the errors introduced by the slow moving region are characterized by two parameters. One parameter is the mean, $\mu_s$, and the other is the standard deviation, $\sigma_s$. When velocity measurements are made the objective remains to calculate a and k. Using error absorption functions requires calculating the parameters that characterize the errors so that the effects of errors are removed. For example, in equation (35) the following parameters are calculated: a, k, $f_f$, $\sigma$, $\mu_s$, and $\sigma_R$. In general, and the case illustrated, multiple measurements of velocity will be available and a statistical method such as least squares or least absolute value will be used to obtain the best fit to the measured data. The equations will, in general, be non-linear and require an implementation of a non-linear fitting technique, such as non-linear least squares.

Figure 14:
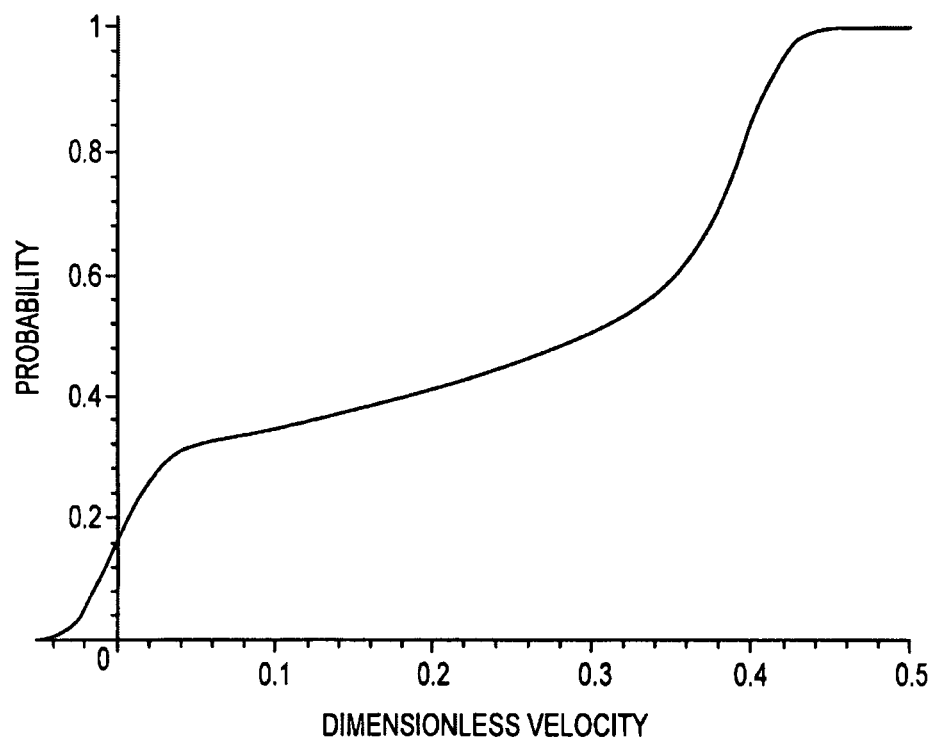
FIG. 14 graphs an example cumulative probability function that includes a slow moving region and noise.

FIG. 14 illustrates a cumulative probability function based on equation (35) for the case when the slow moving mean velocity is zero.

The probability density function associated with equation (35) is given in equation (34):

$$f_{noise,slow}(\phi) = \frac{1}{2}\frac{(1-f_f)\sqrt{2}\,e^{\left(-1/2\frac{(\phi-\mu_s)^2}{\sigma_s^2}\right)}}{\sigma_s\sqrt{\pi}} + \tag{36}$$

$$f_f \int_0^a \frac{\left(1-\frac{x}{a}\right)^{\left(2\frac{1}{k}-1\right)} e^{\left(-1/2\frac{(\phi-x)^2}{\sigma^2}\right)}\sqrt{2}}{\sqrt{\pi}\,\sigma ka} dx$$

Figure 15:
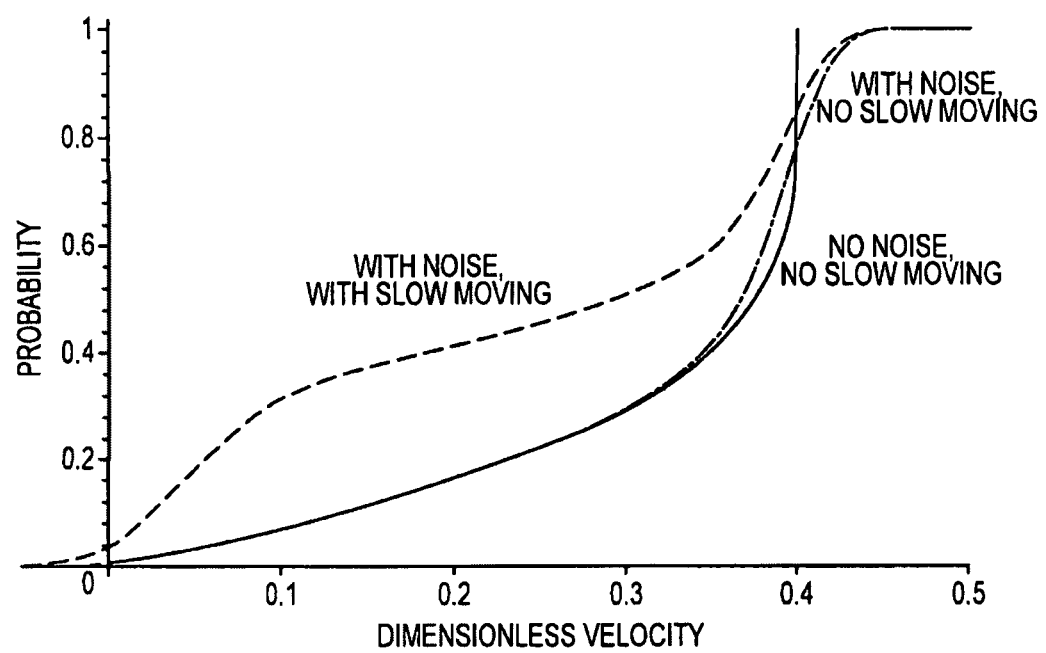
FIG. 15 graphs example cumulative functions with and without sources of error.
Figure 16:
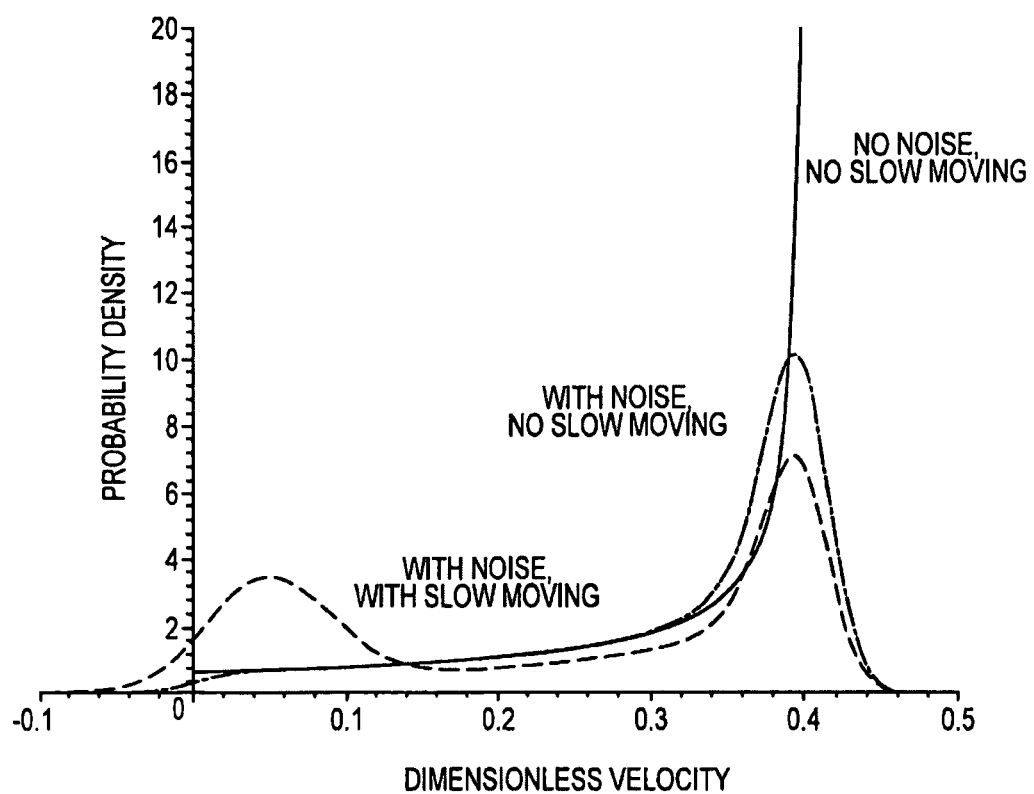
FIG. 16 graphs example density functions with and without sources of error.

FIGS. 15 and 16 are the cumulative and density functions for the case where $f_f$=0.7, $\mu_s$=0.05, $\sigma_s$=0.04, a=0.4, k=8, $\sigma$=0.02. These figures show the dimensionless velocity distribution when there is no measurement noise or slow moving region effects, as well as the distributions as these two sources of errors are introduced. These figures also demonstrate that when the parameters for the error absorption functions are known, the calculated results that become the data without errors can be recovered.

The preceding equations for the density functions and cumulative probability functions can also be used with dimensioned velocity instead of dimensionless velocity. The measured velocity data will have velocity units and are used where the variable $\phi$ appears in the equations. In the following discussion, when either dimensioned velocity or dimensionless velocity may be used the general term "velocity" will be used.

The preceding equations for the density functions have been described as probability density functions. This description is convenient for elucidating the derivation. These density functions are usually referred to as spectral density functions and define the velocity spectra for the measured flow fields. When ultrasonic measurements, including Doppler measurements, are made the frequency spectra may be converted to velocity spectra using standard calculation methods.

In one embodiment of the invention, the measured data may be fit to one or more multi-parameter functions that include parameters for the velocity spectral density and for one or more error absorption functions. In another embodiment of the invention, the measured data may be fit to one or more multi-parameter functions that include parameters for the cumulative velocity spectrum and for one or more error absorption functions. Using the cumulative velocity spectrum instead of the density function reduces the effects of measurement errors because the cumulative spectrum is the smoothed integral of the density function.

When the fitting is done to either a velocity spectral density function or a cumulative velocity spectrum function, the fitting process will determine the values of the parameters that lead to the smallest errors between the measured data and the values predicted by the function. The smallest errors may be those determined using any suitable criteria and include minimizing the sum of least squared errors or minimizing the sum of least absolute value errors. The fitting process may fit all of the parameters as a set or it may first estimate values for the error absorption functions and remove the effects of errors before calculating values for the parameters that define the velocity spectra. The step-wise process of first removing the effects of errors leads to calculating approximately error-free data distributions. The error-free data are the velocity distribution for the material flowing in the channel for which the velocity spectra parameters are desired. The parameters are, for example, a and k calculated using equation (11) for use in equation (17) or equation (18) to calculate τ, from which the radius R is calculated.

During the parameter fitting process an iterative process will generally be used during which values for the parameters are systematically adjusted to obtain the best fits to the velocity data. In one embodiment of the current invention the iterative process systematically selects values for the error absorption parameters to calculate approximately error-free velocity distributions. The approximately error-free distributions are then used to calculate velocity distribution parameters. In the case where the over fit of the function to the measured velocity data is not good enough, the velocity distribution parameters may be used to calculate revised values for the error absorption parameters. The revised error absorption parameters are then used to calculate a revised set of approximately error-free velocity distributions. The revised distribution is then used to recalculate values for the velocity distribution parameters. This iterative process of removing errors and calculating velocity distribution parameters is followed until a suitably good fit to the data occurs. Using this embodiment where errors are first removed from the measured data before the velocity distribution parameters are calculated has the advantage of generally producing better estimates of the velocity distribution parameters in a specified number of iterations. It should be noted that, obtaining accurate estimates of the velocity distribution parameters, such as the a and k in equation (18), is more important than calculating the values of other parameters because it is the velocity distribution parameters that are used to calculate dimensionless time, τ, which then becomes the basis for calculating the flow channel's dimensions.

The method described for reducing or eliminating errors using error absorption functions is ap plicable for use with both dimensionless velocity and dimensioned velocity. When dimensioned velocity, v, is used instead of dimensionless velocity, φ, the parameters associated with velocity have dimensions. For example, when a Gaussian distribution is used the mean and standard deviation will have velocity units. Similarly, velocity profile parameters can have units, as for example, the variable a used above would have velocity units.

After two velocity distributions have been measured and their parameters characterized the values for the variables a, k, $a_t$, and $k_t$ are known and may be used with equation (17) or equation (18) to solve for τ.

It should be noted, however, that solving for τ may be mathematically easier by using a different equation. In this regard, the peak velocity at the time when a velocity profile is measured is $a_t$. $a_t$ is the velocity at the center of the tube, when the radius is zero and ξ=0. Making this substitution into equation (18) produces an equation for $a_t$:

$$a_t = 1 - 2\left(\sum_{n=1}^{N} \frac{\left(\frac{4 - a\alpha(0, n)^2 + a\alpha(0, n)^{(2-k)}}{\text{LommelS1}(k+1, 0, \alpha(0, n))}\right) e^{(-\alpha(0,x)^2 \tau)}}{(J(1, \alpha(0, n))\alpha(0, n)^3)}\right) \quad (37)$$

In this case, equation (38) is the result of starting with equation (16) and solving for $k_t$, assuming a known value, $\phi_i$, for selected values of ξ and φ which can be denoted as $\xi_i$ and $\phi_i$.

$$k_t = \frac{\ln\left(\frac{-\phi_i + a_t}{a_i}\right)}{\ln(\xi_i)} \quad (38)$$

Other than the extremes of $\xi_i=0$ or $\xi_i=1$ which lead to undefined operations, any value may be selected for $\xi_i$, along with the corresponding value for $\phi_i$. Therefore, $\phi_i$ and $\xi_i$ can be any ordered pair on the velocity profile curve. Since we know from equations (16) and (18) that φ is a function of ξ and ξ, $\phi_i$ can be eliminated by substituting into equation (38). The result is equation 39.

$$k_t = \frac{\ln\left(\frac{-\xi_i^2 + 2\left(\sum_{n=1}^{N} \frac{e^{(-\alpha(0,n)^2 \tau)}(J(0, \alpha(0, n)\xi_1) - 1)}{J(1, \alpha(0, n))\alpha(0, n)^3}\right)}{-1 + \left(2\sum_{n=1}^{N} -\frac{\left(\begin{array}{c}(-4 + a\alpha(0, n)^2 - a\alpha(0, n)^{(2-k)})\\ \text{LommelS1}(k+1, 0, \alpha(0, n)))\\ e^{(-\alpha(0,n)^2 \tau)}\end{array}\right)}{(J(1, \alpha(0, n))\alpha(0, n)^3)}\right)}\right)}{\ln(\xi_i)} \quad (39)$$

EQ. 39 gives $k_t$ in terms of the parameters that characterize the initial velocity distribution (a, k), dimensionless time (τ), which is also the time constant, and the selected ξ (which is designated as $\xi_i$) φ is no longer used. This equation implicitly gives τ in terms of $k_t$. Therefore, when an initial velocity profile and a subsequent velocity profile have both been characterized then the value of the time constant τ can be determined. For the calculations, any $\xi_i$ on the open interval (0,1) can be selected. For example, the decision to use $\xi_i=0.9$ can be made. After an explicit value has been assigned to $\xi_i$ the result is an explicit equation that gives $k_t$ for any specified value of τ. For example, if $\xi_i=9/10$ then the result is equation (40). After evaluation, equation (40) becomes equation (41), which can be solved iteratively for τ when values for a, k, and $k_t$ are known. As before, LommelS1 is the Lommel s function.

$$k_t = \frac{\ln\left(-\frac{81}{100} + \frac{\left(2\sum_{n=1}^{N} \frac{e^{(-\alpha(0,n)^2\tau)}\left(J\left(0, \frac{9}{10}\alpha(0,n)\right) - 1\right)\left(\begin{array}{c}(-4 + a\alpha(0,n)^2 - a\alpha(0,n)^{(2-k)})\\ \text{LommelS1}(k+1, 0, \alpha(0,n))\end{array}\right)}{J(1, \alpha(0,n))\alpha(0,n)^3}\right)}{-1 + \left(2\sum_{n=1}^{N} -\frac{\left(\begin{array}{c}(-4+a\alpha(0,n)^2 - a\alpha(0,n)^{(2-k)})\\ \text{LommelS1}(k+1, 0, \alpha(0,n)))\\ e^{(-\alpha(0,n)^2\tau)}\end{array}\right)}{(J(1, \alpha(0,n))\alpha(0,n)^3)}\right)}\right)}{\ln\left(\frac{9}{10}\right)} \quad (40)$$

-continued $$k_t = -9.491221577 \quad (41)$$

$$\ln\left(\frac{-.81 + 2\cdot\left(\sum_{n=1}^{N}\frac{e^{(-\alpha(0,n)^2\tau)}\left(J\left(0,\frac{9}{10}\alpha(0,n)\right)-1\right)}{J(1,\alpha(0,n))\alpha(0,n)^3}\right)}{-1.+2\left(\sum_{n=1}^{N}-\frac{\begin{pmatrix}(-4+a\alpha(0,n)^2-a\alpha(0,n)^{(2-k)})\\\text{LommelSl}(k+1,0,\alpha(0,n)))\\e^{(-\alpha(0,n)^2\tau)}\end{pmatrix}}{J(1,\alpha(0,n))\alpha(0,n)^3}\right)}\right)$$

Calculating the Lommel s function is time consuming and difficult to do precisely. Accordingly, one aspect of the present invention is precalculating the values for one or more terms in equations that implicitly define $\tau$ in terms of the velocity profile characterization parameters and then using these precalculated values in a simplified equation that is used to develop an interpolating function that can be used to calculate the value for the time constant $\tau$. The following is an example of how this aspect of the present invention is implemented. In this example, equation (41) can be used to precalculate values for its summation terms and these precalculated values used in a simplified equation to develop an interpolating function that relates $k_t$ to $\tau$ When numerical values for $\tau$ and $k$ are substituted into equation (41) the result is an equation for $k_t$ in terms of a. For example, if $\tau=0.1$ and $k=12$ then equation (41) becomes equation (42):

$$k_t = \quad (42)$$
$$-9.491221577 \ln\left(.01000000000\frac{-27.73984105 - 70.73715877a}{-.3851895036 - .8293031252a}\right)$$

Equation (42) has the form of equation (43). Equation (39) and equations based on it, such as equation (41), can be converted into the form of equation (43).

$$k_t = A\ln\left(\frac{B + Ca}{D + Ea}\right) \quad (43)$$

where $$A = \frac{1}{\ln(\xi_i)} \quad (44)$$

$$B = -\xi_i^2 - 8\left(\sum_{n=1}^{N}\frac{e^{(-\alpha(0,n)^2\tau)}(J(0,\alpha(0,n)\xi_i)-1)}{J(1,\alpha(0,n))\alpha(0,n)^3}\right) \quad (45)$$

$$C = -2\left(\sum_{n=1}^{N}\frac{\begin{pmatrix}(-\alpha(0,n)^2+\alpha(0,n)^{(2-k)})\\\text{LommelSl}(k+1,0,\alpha(0,n)))\\e^{(-\alpha(0,n)^2\tau)}(J(0,\alpha(0,n)\xi_i)-1)\end{pmatrix}}{J(1,\alpha(0,n))\alpha(0,n)^3}\right) \quad (46)$$

$$D = -1 + 8\left(\sum_{n=1}^{N}\frac{e^{(-\alpha(0,n)^2\tau)}}{J(1,\alpha(0,n))\alpha(0,n)^3}\right) \quad (47)$$

$$E = 2\left(\sum_{n=1}^{N}\frac{\begin{pmatrix}(-\alpha(0,n)^2+\alpha(0,n)^{(2-k)})\\\text{LommelSl}(k+1,0,\alpha(0,n)))\\e^{(-\alpha(0,n)^2\tau)}\end{pmatrix}}{J(1,\alpha(0,n))\alpha(0,n)^3}\right) \quad (48)$$

A will always be the same once $\xi_i$ has been selected. B and D will be constant for any selected $\tau$. Although values can be calculated at any time, the preferred method is to select values for $\tau$ and k before measurements are needed and calculate and store values for B, C, D, and E ahead of time in a table. For example, the values could be stored in a lookup table that is convenient for rapid access, such as if the entries are indexed by values of $\tau$ and k. Using this approach, solving for $\tau$ starts by selecting an assumed value for $\tau$ and using the lookup table entries that bracket the actual value for k and the assumed value for $\tau$ and calculate a value for $k_t$ using the actual value for a. Select a set of assumed values for $\tau$ and calculate additional values for $k_t$. The result is a table that relates $k_t$ and $\tau$. In this regard, a suitable interpolating function may be used, such as an interpolating polynomial, to relate $\tau$ and $k_t$. The interpolating function may then be used to solve for $\tau$ using the actual value for $k_t$.

The derivation and description of the method for the efficient solution of $\tau$ described above used $\xi$ and dimensionless velocity. The same derivation and description of the method for efficient solution of $\tau$ also applies using $\xi$ and dimensioned velocity. The results using dimensioned velocity are identical except that the velocity profile parameter a includes velocity dimensions.

Another aspect of the present invention is to identify the presence and nature of periodic and non-periodic flow rate behavior from one or more VFRs and the time intervals associated with the velocity profiles used to calculate the VFRs. The means used to identify the presence and nature of periodic flow rate behavior includes mathematical means such as Fourier analysis, artificial intelligence, statistical analysis, and non-linear analysis including those used in complexity theory and analysis. Identification of the presence and nature of the periodic flow rate behavior includes identifying changes in flow rate that reveal the cyclic behavior of flow, including the pumping cycle period from the heartbeat rate of living patients.

Another aspect of the present invention is to use one or more VFRs in conjunction with one or more of the time intervals between velocity measurements to calculate the fluid volume that has flowed during the time elapsing between one or more time intervals. Such calculations are particularly advantageous when cyclic flows occur, such as when blood flows from a heart. Such calculations may be used to determine the blood volume delivered per cycle when the pumping cycle period is used in conjunction with data that relates fluid volume delivery with time. The heartbeat rate used to determine the volumetric delivery per heartbeat or other cycle may be an exogenous input such as a parameter entered by a user or data from an external source, such as an EKG, or it may be based on the identification of the presence and nature of the periodic and non-periodic flow rate behavior as described above. Volumetric delivery is a derived parameter.

Another aspect of the present invention is to use volumetric delivery data per heartbeat in conjunction with total left ventricle volume to calculate ejection fraction. Total left ventricle volume may be estimated using means such as an interrogating signal that evaluates the nature or the signal returned from turbulent flow sections of a region energized by the interrogating signal. Ejection fraction is a derived parameter.

For purposes of illustration, the following description is related to a specific medical device application, although it will be appreciated that the present system is both useful for and readily employable in applications beyond the specific medical device application described. As will also be appreciated, the present invention may take on configurations other than those described and illustrated. For example, the means used for calculations may combine or separate functional units in configurations other than those described. As another example, the sequence of calculations may be done differently than those described.

Figure 17:
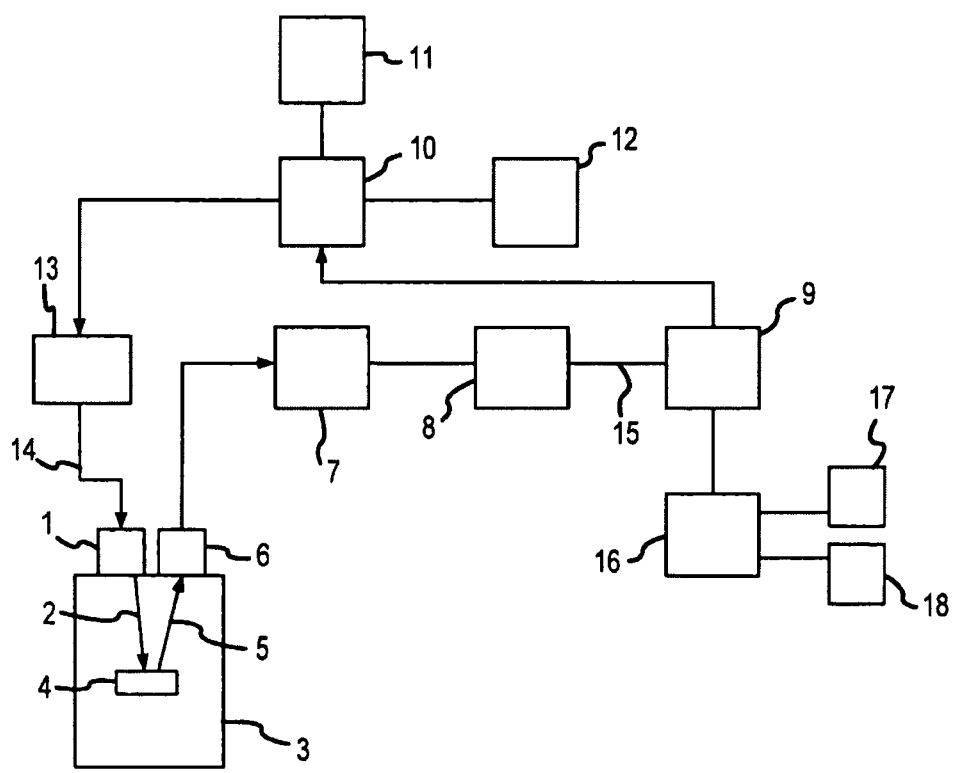
FIG. 17 illustrates a block diagram of one embodiment of a system.

FIG. 17 illustrates a system that uses an ultrasonic transducer 1 to introduce an interrogating signal 2 into a patient 3. The transducer may be any of various conventional ultrasound units and may provide the signal 2 in the form of a pulse train. In accordance with the present invention, the transducer 1 may be disposed external to the patient 3, for example, in the suprasternal notch and may be directed so that the signal targets the ascending aorta. Depthwise targeting can be accomplished by processing return signal components received during the time window corresponding to the desired depth.

The interrogating signal 2 backscatters from patient tissues 4 and a return signal 5 is detected by the receiving transducer 6. The receiving transducer 6 converts the mechanical energy (not shown) of the return signal 5 into oscillating electrical signals (not shown) that are introduced into the analog amplification and processing module 7. This module may perform a variety of functions including analog digital conversion, amplification, filtering and other signal enhancement. The output from the analog amplification and processing module 7 is a digitized stream of data that is the input to the digital processing module 8. The digital processing module 8 converts the digitized signal data into frequency spectra, using known mathematical processes such as a fast fourier transform, and then into velocity data which becomes velocity vectors that the digital processing module 8 stores as vectors of digital dimensioned velocity profile data in a memory location (not shown) of the data processing module 9. The data processing module 9 converts the velocity profile data (not shown) into a data vector (not shown) that represents a piecewise continuous dimensioned velocity spectral density function. Further processing of the density function data vector is described in more detail later.

The digital processing module 8 may contain one or more microprocessors and one or more data storage means that enable it to make the calculations needed to determine VFRs and derived parameters. The data storage means contains values for parameters used in look-up tables that facilitate calculations that avoid or reduce the need to evaluate special functions. Additionally, certain values such as a channel dimension, average flow rate or the like may be predetermined and stored in cache or other storage for combination with values obtained in connection with a later measurement process. FIG. 17 also illustrates that the system has a control module 10 that receives setup parameters (not shown) from the user 11. Setup parameters can include data such as patient parameters, e.g., hematocrit, and on/off signals regarding when data reading and processing should begin and end. The control module 10 receives signals from the data processing module 9 regarding the status of the received data (not shown) and changes in the interrogating signal 2 that are needed to improve or maintain quality measurement data. The control module 10 optionally receives signals of biological activity 12, such as electrical signals related to cardiac activity. The biological signals 12 may be used to synchronize interrogating signals 2 to biological functions or to correlate calculated values such as VFRs to such biological functions. The control module 10 signals the transducer power module 13 when the interrogating signal 2 should begin and end. The transducer power module 13 provides the drive signal 14 to the ultrasonic transducer 1. The data processing module 9 generates output data 15 that go to the output module 16.

The output module 16 generates visible displays 17 and audio devices 18 to inform the user of the system's operating status and the results of the system's interrogation of the patient 3. The output module 16 may also include ports for providing data to other instruments (such as an EKG) or processing systems, for example, via a LAN or WAN. It will be appreciated that the various processing modules described above may be embodied in one or more computers, located locally or interfaced via a network, configured with appropriate logic to execute the associated algorithms. Additionally, certain signal drive and processing components may be incorporated into the interrogating signal instrument such as an ultrasound system.

Figure 18:
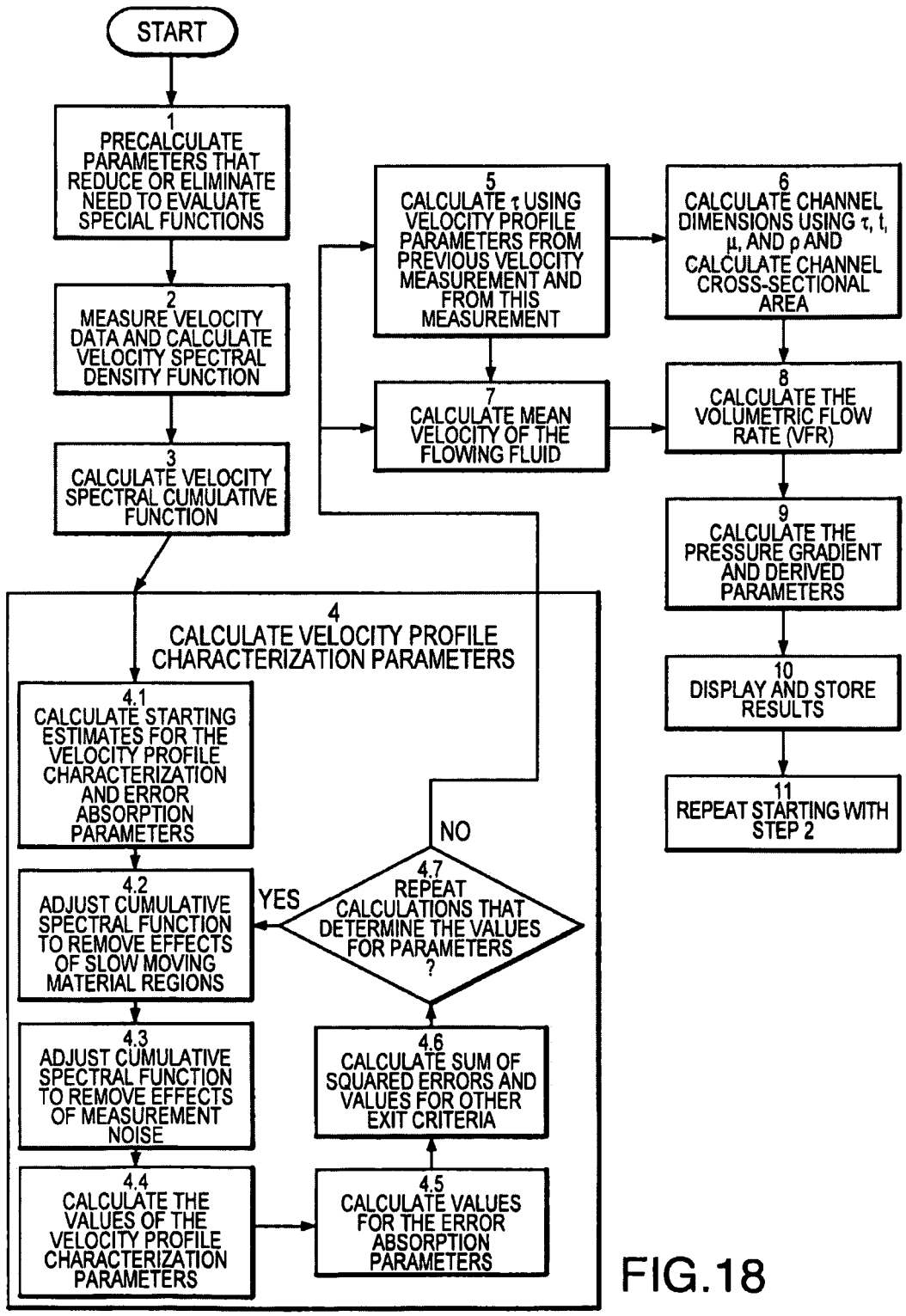
FIG. 18 illustrates one embodiment of the calculation sequence.

In one embodiment of the method of the present invention the calculation of VFR and derived parameters proceeds as illustrated in FIG. 18.

Step 1. Precalculate parameters that reduce or eliminate the need to evaluate special functions. In this regard, step 1 may include calculating and storing for later use the values for the variables A, B, C, D, and E used in equation (43). Calculating the values for the variables using equations (44) through (48). The preferred value for the summation limit N is a value larger than four, and more preferably for N to be larger than eight, and even more preferably for N to be larger than 12. A value of 50 has been found to provide suitable results when the values for the variables are pre calculated using the mathematical software package Maple that is sold by Waterloo Maple, Inc., Waterloo, Ontario, Canada. The precalculated values are then incorporated into software that makes the calculations needed to calculate channel dimensions, VFRs, and derived parameters.

The stored values for the variables will be used to generate functions that relate $k_r$ and $\tau$ with either no need or a reduced need to evaluate special functions. It is preferable to use non-uniform spacing between the values of the $\tau$ and k used to calculate the values of the stored variables used in the data used to calculate functions that avoid or reduce the need to evaluate special functions. It is even more preferable to use spacings for $\tau$ and k that increase as the values for $\tau$ and k increase. It is still more preferable for the spacings for $\tau$ and k to increase exponentially starting from the smallest values for $\tau$ and k. Such exponential growth can come from having each successive value being a constant multiple of the previous value. Select the number of $\tau$ to have and the number of k to have and also select growth factors for them. For calculating flow in the ascending aorta of humans the values of parameters used in the calculations are:

number of $\tau$: in the range of 2 to 100 are preferable and in the range of 5 to 50 even more preferable with a range of 15 to 25 being still more preferable starting value for $\tau$: being larger than −1 and smaller than 1 is preferable, with a value larger than 0 and smaller than 0.1 being more preferable with a starting value in the range of 0 and 0.01 being still more preferable, with a starting value with an order of magnitude of 0.001 being still more preferable.

size of each successive $\tau$: in the range of 1.001 to 10 times the size of the preceding value being preferable and in range of 1.01 to 5 times the size of the preceding value being more preferable with a range of 1.1 to 2 times the size of the preceding value being even more preferable, with a value of about 1.5 times the size of the preceding value being still more preferable.

number of k: in the range of 2 to 100 are preferable and in the range of 5 to 50 even more preferable with a range of 15 to 25 being still more preferable.

starting value for k: a value larger than 0 and smaller than 100 being preferable, with a starting value larger than 1 and smaller than 10 being more preferable and starting value between 1.5 and 2.5 being even more preferable and a value of about 2 being still more preferable.

size of each successive k: in the range of 1.001 to 10 times the size of the preceding value being preferable and in range of 1.01 to 5 times the size of the preceding value being more preferable with a range of 1.1 to 2 times the size of the preceding value being even more preferable, with a value of about 1.125 times the size of the last value being still more preferable.

For the special case of $\tau=0$ no entries are needed because in this case $k_\tau = k$. The final value of $\tau$ used to precalculate variables depends upon the nature of the fluid flow system. The largest $\tau$ for which calculations are needed exists. A largest $\tau$ smaller than 100 is preferable as very little increased resolution exists beyond this limit. Further, limiting the size of the precalculated data allows more resolution at smaller $\tau$ for the same data storage size. A largest $\tau$ smaller than 10 is even more preferable and a largest $\tau$ smaller than 2 is even more preferable.

The smallest possible value for k is 2 so the preferred lower limit for k is 2. The lower limit for the largest value for k is preferably between 3 and 20. More preferably, the lower limit for the largest value for k is larger than about 7 to 20. As k gets large the velocity profile becomes very flat. The preferable upper limit for the largest k is 1,000,000 and an even more preferable limit for k is 1,000, and a still more preferable upper limit on k is 100.

Step 2. Measure velocity data and calculate the velocity spectral density function.

Obtain measured velocity data and calculate the measured velocity spectral density function using suitable means such as Fourier analysis. In on example of the present invention, the measured velocity data may be obtained using an ultrasonic interrogating signal. Designate the number of velocities included in the spectral density function as N. Designate each of the N ordered pairs of the density function as $(v_j, f_j)$.

Step 3. Calculate spectral cumulative function.

Figure 19:
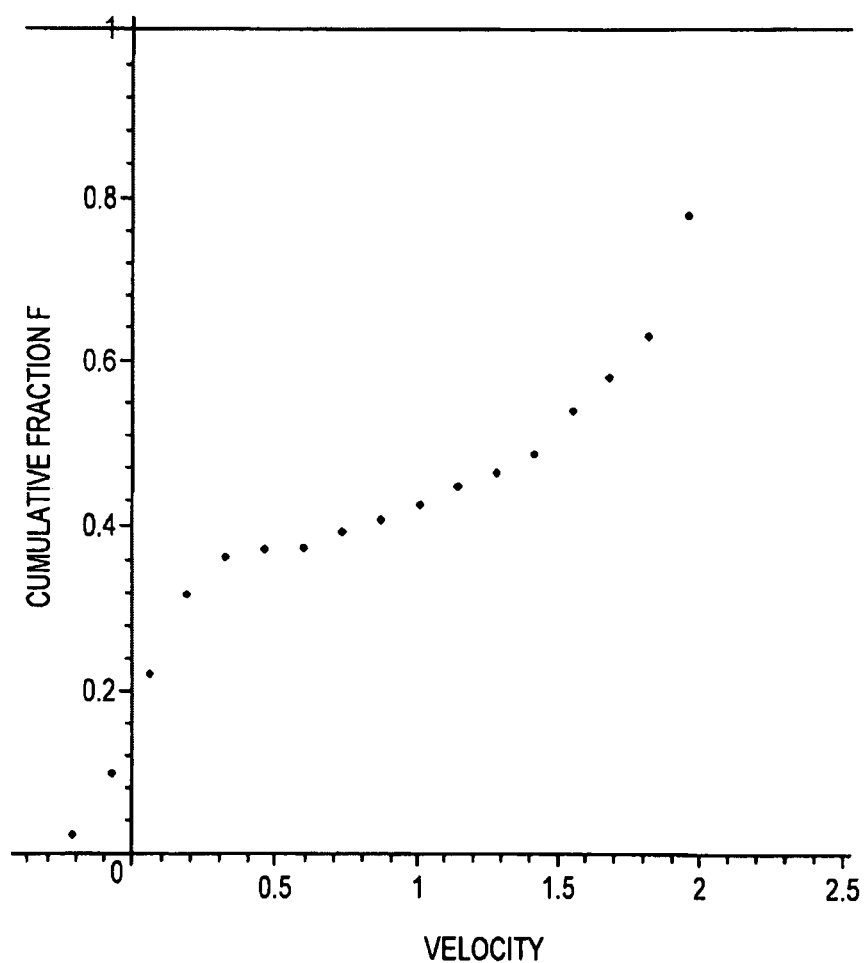
FIG. 19 illustrates an example of spectral cumulative data points.

Use the density function data to calculate a cumulative function by numerically integrating the area under the density function using a suitable numerical integration method such as Simpson's rule and normalizing the N distinct integration results by dividing by the total area under the density function. The result is N ordered pairs that have a range defined on the interval [0,1]. Designate each of the cumulative function order pairs as $(v_j, F_j)$. FIG. 19 illustrates an example of a graph of $(v_j, F_j)$ data.

Step 4. Calculate velocity profile characterization parameters.

The description in this embodiment assumes that the flow system may be modeled using a cylindrical channel and that the pressure gradient may change without changing direction.

Step 4.1 Calculate starting estimates for the velocity profile characterization and error absorption parameters.

For this embodiment the parameters for which initial estimates are needed are $f_f$, $\mu_s$, $\sigma_s$, $\sigma$, a, and k. Generate starting values using the following procedure.

$\sigma$: Numerically search the spectral density function until two values of velocity (either v or $\phi$) find the that correspond to the inflection points of the right-side mode and then take $\sigma_{initial\ guess} = 0.925(\phi_{right\ mode_{right\ inflection\ point}} - \phi_{right\ mode_{left\ inflection\ point}})$. Find the inflection points by taking second differences of the cumulative probability function (which will be the numerical equivalent of finding the slope of the velocity spectral density function) and, working backwards from large to small $\phi$, find (1) the minimum value that occurs when the second difference becomes less than 0 and (2) the maximum while the second difference is greater than 0 before the second difference again takes on values <0. These two values of $\phi$ will give the two inflection points and the peak will be between these two inflection points. Assume that the peak is equidistant between the inflection points and that the shape of the peak is approximately normal. These assumptions mean that the two inflection points are spaced $2\sigma$ apart. Calculate $\sigma$ by dividing the distance between the two inflection points by two.

$f_f$: Assuming that the flowing velocities will generally not be less than zero, and that the noise from measuring the flowing velocities will generally not demote measurements to become less than zero, assume that all of the $\phi<0$ are due to non-flowing elements. It should be noted that this assumption is only used to develop a starting estimate form and the solution to the equation after doing the least squares fit does not depend on this assumption being true. Search the spectral density function starting with the lowest values for $\phi$ and locate the value of $\phi$ that corresponds to the left-side mode's peak. The value of the cumulative distribution, $F(\phi)$, at this value will be ½ of the value of $(1-f_f)$.

$\mu_R$: Use the value of $\phi$ that goes with the peak of the left-side mode.

$\sigma_s$: find the inflection points of the left-side mode and take $\phi_{s_{initial\ guess}} = 0.925(\phi_{left\ mode_{right\ inflection\ point}} - \phi_{left\ mode_{left\ inflection\ point}})$. This uses the same logic as was developed for $\sigma_{initial\ guess}$. There may be a problem with the right inflection point being polluted with data spilling over from the flowing data, in which case use $\sigma_{s_{initial\ guess}} = 0.925(\phi_{left\ mode_{right\ inflection\ point}} - \phi_{left\ mode_{peak}})$. The underlying assumption is that the distribution of the left-side mode can be approximated as being a normal distribution. The inflection points for a normal distribution are one standard deviation from the mean.

Estimate initial estimates for $v_0$ and k by following Steps 4.2 through 4.4, below. Then, without changing the initial estimates for $v_0$ (which will be used as the value for a) and k and starting with the initial estimates for $f_f$, $\mu_s$, $\sigma_s$, and $\sigma$, improve the estimates for $f_f$, $\mu_s$, $\sigma_s$, and $\sigma$. The improved values are those values that minimize the sum of squared errors calculated as the difference between the actual $F_n$ and that predicted by equation (35). A multidimensional numerical function minimization method of the kind well known in the art may used.

Step 4.2. Adjust the cumulative spectral function to remove the effects of signals from slow moving material regions. Adjust the measured values for $F_j$ to remove the effects of slow moving material echoes. With estimates of $(f_f, \mu_s, \sigma_s)$ adjust for the effect of the slow moving material by substituting $\phi = v_j$ and $F_j$ into equation (49), below, and calculating $F_{no\_slow_j}$ for each $(v_j, F_j)$.

$$F_{no\_slow_j} = \frac{F_j - (1-f_f)\left(\frac{1}{2}\mathrm{erf}\left(\frac{1\sqrt{2}(-\phi+\mu_s)}{2\sigma_s}\right) + \frac{1}{2}\right)}{f_f} \quad (49)$$

The $$(1-f_f)\left(-\frac{1\ \text{erf}\left(\frac{1\sqrt{2}\,(-\phi+\mu_s)}{2\sigma_s}\right)}{2}+\frac{1}{2}\right)$$

term removes the offset caused by the slow moving material. Dividing by $f_f$ re-normalizes the data to the correct scale. The result leaves the $F_j = F_{no\_slow_j}$ for the flowing material combined with the measurement noise effect caused by σ.

Step 4.3. Adjust cumulative spectral function to remove the effects of measurement noise.

Using $F_j = F_{no\_slow_j}$, correct for the effects of measurement noise by using equation (50).

$$F_{no\_noise_j} = 2F_j - \frac{1}{2}(-F_j+1)^{\left(-\frac{\ln(a)}{\ln\left(\frac{\phi_j+a}{a}\right)}\right)}$$ (50)

$$\int_0^{(-F_j+1)^{\left(\frac{\ln(a)}{\ln\left(\frac{\phi_j+a}{a}\right)}\right)}} \text{erf}\left(\frac{1}{2}\frac{\sqrt{2}\left(\phi_j+t^{\left(\frac{\ln\left(\frac{-\phi_j+a}{a}\right)}{\ln(-F_j+1)}\right)}-a\right)}{\sigma}\right)+1\,dt$$

Designate the results of this calculation as $(v_n, F_n)$. The $F_n$ have been adjusted to remove the effects of the slow moving material and of measurement noise.

Step 4.4. Calculate the values of the velocity profile parameters. Calculate k and $v_0$. In this embodiment those parameters are a and k in equation (11). Do a least squares fit that uses the $(v_n, F_n)$ to calculate values for k and a.

4.4.1 Renormalize the set of $(v_n, F_n)$ if the largest $F_n > 1$ and continue to designate the set of N sets of ordered pairs as $(v_n, F_n)$.

4.4.2 Using the N ordered pairs of data do a least squares fit to calculate k and a. In this case, the data being used are dimensioned velocity. Therefore, the value calculated for a will have units and be the largest velocity that existed at the time of the velocity measurement. Designate this largest velocity as $v_0$. The following steps implement the least squares fit that calculate k and $v_0$.

4.4.2.1. Use equation (51) to calculate $G_n$ for each of the $(v_n, F_n)$.

$$G_n = -F_n + 1$$ (51)

4.4.2.2 Find k by finding the root of equation (52). The variables A, B, C, and D are defined in equations (53) through (56). Use a numerical search procedure. Preferably, the search routine will use a lower bound of k=2 and an upper bound that is preferably greater than 2 and a large number in the range of about 20 to 1,000,000 to bound the root.

$$0 = \frac{\left[\sum_{n=1}^{N}\ln(G_n)\left(G_n^{\left(\frac{1}{2}k\right)}v_nN - 2G_n^{\left(\frac{1}{2}k\right)}v_nA + G_n^{\left(\frac{1}{2}k\right)}v_nB - G_n^{\left(\frac{1}{2}k\right)}\right.\right.}{(N-2A+B)^2}$$

$$\left.\left. D + G_n^{\left(\frac{1}{2}k\right)}C + G_n^k D - G_n^k C\right)\right]$$ (52)

$$A = \sum_{n=1}^{N} G_n^{(1/2k)}$$ (53)

-continued $$B = \sum_{n=1}^{N} (G_n^{(1/2k)})^2$$ (54)

$$C = \sum_{n=1}^{N} G_n^{(1/2k)} v_n$$ (55)

$$D = \sum_{n=1}^{N} v_n$$ (56)

4.4.2.3. Use equation (57) to calculate $v_0$ using the N values of $(v_n, G_n)$ and the value of k calculated in the preceding step.

$$v_0 = \frac{-\left(\sum_{n=1}^{N} v_n\right) + \left(\sum_{n=1}^{N} G_n^{(1/2k)} v_n\right)}{-N + 2\left(\sum_{n=1}^{N} G_n^{(1/2k)}\right) - \left(\sum_{n=1}^{N} (G_n^{(1/2k)})^2\right)}$$ (57)

4.5. Calculate values for the error absorption parameters.

For this embodiment the parameters for which values are to be calculated are $f_f$, $\mu_s$, $\sigma_s$, and σ. Using the values for $v_0$ (which will be used as the value for a) and k that were calculated in step 4.4.2.3, calculate values for $f_f$, $\mu_s$, $\sigma_s$, and σ that minimize the sum of squared errors calculated as the difference between the actual $F_n$ and that predicted by equation (35). Again a multidimensional numerical function minimization method of the kind well known in the art may be used.

4.6. Calculate Sum of Squared Errors and values for other exit criteria.

The multidimensional numerical function minimization method employed will require calculating the size of errors and the amount of change in the parameters for $f_f$, $\mu_s$, $\sigma_s$, σ, a, and k. The preferred approaches will calculate changes in at least a and k.

4.7. Check whether calculations that determine the values for parameters need to be repeated.

If the sum of squared errors has continued to decrease significantly or if the values of a and k have continued to change by more than a suitable tolerance then the calculations starting with step 4.2 should be repeated. If the values for a or k change from one iteration to the next by more than 10 percent then it is preferred that another iteration be done. It is more preferable that if the values for a or k change from one iteration to the next by more than one percent that another iteration be done.

Figure 20:
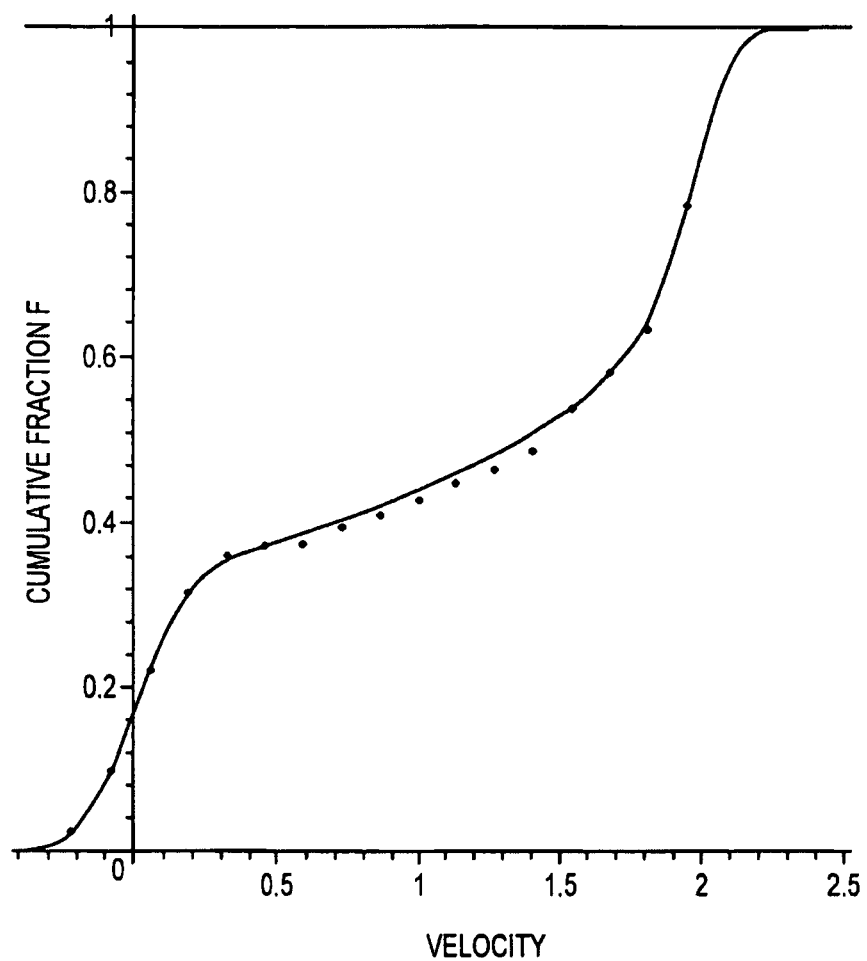
FIG. 20 illustrates an example of spectral cumulative data point fitting in progress.

FIG. 20 illustrates how a cumulative distribution that is in the process of being fitted to measured data can appear. As more iterations are used to refine the values for the parameters the curve will more closely correspond to the data.

A refinement of the embodiment described above for Step 4 is to select a subset of the N ordered pairs and use these data to make initial calculations. Using a subset of data will make calculations proceed more quickly than if a full set of data is used. The subset of data will produce approximate values for the parameters being calculated. The approximate values can be refined by using more, or all, of the data in subsequent calculations.

A further refinement of Step 4 is:

a. Make initial estimates of all the parameters.

b. Using minimizing the sum of squared errors as the criteria, determine better values of each of $f_f$, $\mu_s$, $\sigma_s$ doing one-dimensional searches for each variable. During these searches do not change the values for a, k, or σ.

c. Using the best values so for $f_f$, $\mu_s$, $\sigma_s$, σ follow the procedure described above to adjust $F_j$ and calculate new values for k and $v_0$ (which is the same as a).

d. Using minimizing the sum of squared errors as the criteria, determine a better value for σ. Again, do not allow the values of a or k to be changed.

e. Using minimizing the sum of squared errors as the criteria, use a multidimensional search to determine improved values for all parameters as a set, except k. This set of values does not allow the value for k to be changed (it uses the value of k that has been most recently calculated), but it does allow extrapolated values for all of the other parameters, including a to be created.

f. Using minimizing the sum of squared errors as the criteria, use one dimensional searches on each parameter to determine improved values (e.g., go back to step b of this further refinement).

Step 5. Calculate τ using velocity profile parameters from previous velocity measurement and from this measurement. For this embodiment, calculate τ using the k and $v_0$ from the previous velocity measurement and the k from the current velocity measurement. (If only one velocity measurement has been made, then skip the rest of the steps and go back to step 2).

Using equation (42) and the variables defined in equation (44) through equation (47) along with the value of k and a from the previous velocity profile (a will be the value of $v_0$ for this embodiment) and the current value for k (which is the value assigned to $k_t$) calculate τ. The values for a and k will fall within the ranges used for the calculations made during Step 1. Find the two values of a used in Step 1 that are above and below the value of a from the measured velocity distribution. Also select the next value of a used in the precalculations that is lower than one that is adjacent to the value of a from the measured velocity distribution. Therefore, three values of a used during Step 1 will be selected. Select values of k from Step 1 that straddle the value of k from the measured velocity distribution. Select a third k used during Step 1 that is next to the one that is less than the a calculated for the actual velocity distribution. For each of the nine combinations of a and k that were used in Step 1 use the values for A, B, C, and D to make nine equations that calculate k, from values of τ. Select an assumed value for τ and calculate values for $k_t$. Use interpolating polynomials to calculate the estimated value for $k_t$ based on the actual values of a and k for the measured distribution. The result is a value of $k_t$ that corresponds to an assumed value of τ. Assume another value for τ and, using the same interpolation process, calculate a second value for $k_t$. Repeat the process a third time to obtain a third set of values for τ and $k_t$. These three data points relate $k_t$ to τ. Use these values to calculate the coefficients of an interpolating polynomial that relates $k_t$ to τ. The actual value of $k_t$ for the most recently measured velocity profile is known, so use the interpolating polynomial to directly solve for the value of τ that produces the known value of $k_t$.

If the assumed values for τ that were used did not straddle the calculated value then the process is repeated. If the assumed values for τ are more than 10 percent different than the calculated value for τ then the process is repeated. The final result is the value of τ that is needed for the initial velocity distribution to change into the second velocity distribution.

Step 6: Calculate channel dimensions using τ (the value of the time constant), ρ (the fluid density), μ (fluid viscosity), and t (the time elapsed between measurements of the fluid velocity). Using known values for each of the variables, use equation (4) to calculate the radius, R. In this embodiment R is the only parameter that characterizes channel dimensions. Calculate the channel's cross-sectional area using the now known value for its radius.

Calculations may be made using measured values of fluid viscosity or density. Alternatively, the calculations may be based on default values, or values based on patient characteristics, such as sex, age, or correlations with hematocrit. Kinematic viscosity can be used instead of separate values for fluid viscosity and density. Kinematic viscosity is less variable than viscosity and this will lead to reduced errors and better correlations to other factors, such as hematocrit.

Step 7: Calculate the mean velocity profile for the flowing fluid.

For this embodiment, calculate the mean velocity using equation (25) and the most recently calculated values for a (which is the most recently calculated $v_0$) and k.

Step 8: Calculate the volumetric flow rate.

Multiply the mean fluid velocity times the cross-sectional area to calculate the volumetric flow rate.

Step 9. Calculate the pressure gradient and derived parameters.

At this point all of the data are known to allow calculating pressure gradient, and other derived parameters, such as changes in velocity, changes in radius as a function of pressure gradient, volume delivered. When external data, such as EKG signals, are available other derived parameters can be calculated, such as correlating EKG signals with velocity and volume delivered.

Step 10: Display and store the results.

Step 11: The entire process of obtaining velocity measurements and conducting the calculations can be repeated. Initial values for various calculations, where searches are needed minimize the sum of squared errors or to find roots, can be based on the most recently calculated values for the parameters.

The above-described elements can be comprised of instructions that are stored on storage media. The instructions can be retrieved and executed by a processing system. Some examples of instructions are software, program code, and firmware. Some examples of storage media are memory devices, tape, disks, integrated circuits, and servers. The instructions are operational when executed by the processing system to direct the processing system to operate in accord with the invention. The term "processing system" refers to a single processing device or a group of inter-operational processing devices. Some examples of processing systems are integrated circuits and logic circuitry. Those skilled in the art are familiar with instructions, processing systems, and storage media.

Those skilled in the art will appreciate variations of the above-described embodiments that fall within the scope of the invention. As a result, the invention is not limited to the specific examples and illustrations discussed above, but only by the following claims and their equivalents.

What is claimed is:

1. An apparatus for use in analyzing physiological material within an organism, comprising:

input structure for receiving input flow velocity information regarding a flow velocity, or derivative thereof, of a physiological fluid in a flow channel of an organism based on an analysis of a flow in said flow channel, said flow velocity information pertaining to a portion of said flow channel having a nonzero velocity;

logic for deriving channel dimension information based on said input flow velocity information independent of any separately obtained dimensional information regarding said flow channel; and output structure for providing an output based on said channel dimension information.

2. An apparatus as set forth in claim 1, wherein said input structure is operative for obtaining information related to at least one velocity profile of said flow channel, where said velocity profile defines a spatial velocity distribution within said flow channel.

3. A computer program device for enabling a computer system to analyze physiological material within an organism, comprising:

logical instructions for enabling the computer system to perform predetermined operations; and a non-transitory computer readable medium having instructions thereon which, when executed by said computer system enable said computer system to perform said predetermined operations including:

obtaining flow velocity information, regarding flow velocity or a derivative thereof, for a flow of a physiological fluid in a flow channel of said organism based on an analysis of said flow; and using said flow velocity information for a portion of the flow channel having a nonzero flow velocity to obtain processed information of a dimension of said flow channel.

4. A device as set forth in claim 3, wherein said operation of obtaining flow velocity information comprises obtaining information related to at least one velocity profile of said flow channel, where said velocity profile defines a spatial velocity distribution within said flow channel.

5. A device as set forth in claim 3, wherein said operation of obtaining flow velocity information comprises performing a measurement using a sensor disposed external to said organism.

\* \* \* \* \*